United States Patent
Perdomini et al.

(10) Patent No.: US 6,482,008 B2
(45) Date of Patent: *Nov. 19, 2002

(54) PROCESS FOR DEVITALIZING TEETH USING HIGH-FREQUENCY ELECTRIC CURRENT

(76) Inventors: Enrico Perdomini, Via R. Di Lauria, 2, Milano (IT); Vittorio Sacchi, Via Masotto, 12, Milano (IT)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/194,810
(22) PCT Filed: Jul. 2, 1996
(86) PCT No.: PCT/IT96/00137
  § 371 (c)(1),
  (2), (4) Date: Dec. 2, 1998
(87) PCT Pub. No.: WO97/46170
  PCT Pub. Date: Dec. 11, 1997

(65) Prior Publication Data
US 2002/0055085 A1 May 9, 2002

(30) Foreign Application Priority Data
Jun. 7, 1996 (IT) .......................................... MI96/A1167

(51) Int. Cl.$^7$ ............................. A61C 5/02; A61C 19/00
(52) U.S. Cl. ......................................... 433/224; 433/32
(58) Field of Search ................................. 433/224, 102, 433/32; 606/41, 44, 46, 48, 49

(56) References Cited

U.S. PATENT DOCUMENTS

| | | | | |
|---|---|---|---|---|
| 1,713,971 A | * | 5/1929 | Lowry et al. | 433/224 |
| 4,944,678 A | * | 7/1990 | Villette | 433/224 |
| 5,295,833 A | * | 3/1994 | Chihiro et al. | 433/224 |
| 5,421,727 A | * | 6/1995 | Stevens et al. | 433/224 |

FOREIGN PATENT DOCUMENTS

| | | | |
|---|---|---|---|
| EP | 392518 | * | 10/1990 |
| NL | 39132 | * | 10/1936 |

* cited by examiner

*Primary Examiner*—John J. Wilson
(74) *Attorney, Agent, or Firm*—Michael J. Striker

(57) ABSTRACT

Process for devitalizing a tooth by transmission of a high-frequency electric pulse to the vascular and nervous tissue in the root canal by insertion in said canal of an electrode in the form of a needle (100), said pulse being generated by an electronic apparatus (10), values of power, time and frequency of said electric pulse being automatically regulated by the electronic apparatus in accordance with the control given by pressing one or another of four push buttons (30–33) one for each of the different types of teeth.

12 Claims, 25 Drawing Sheets

Figure 1:
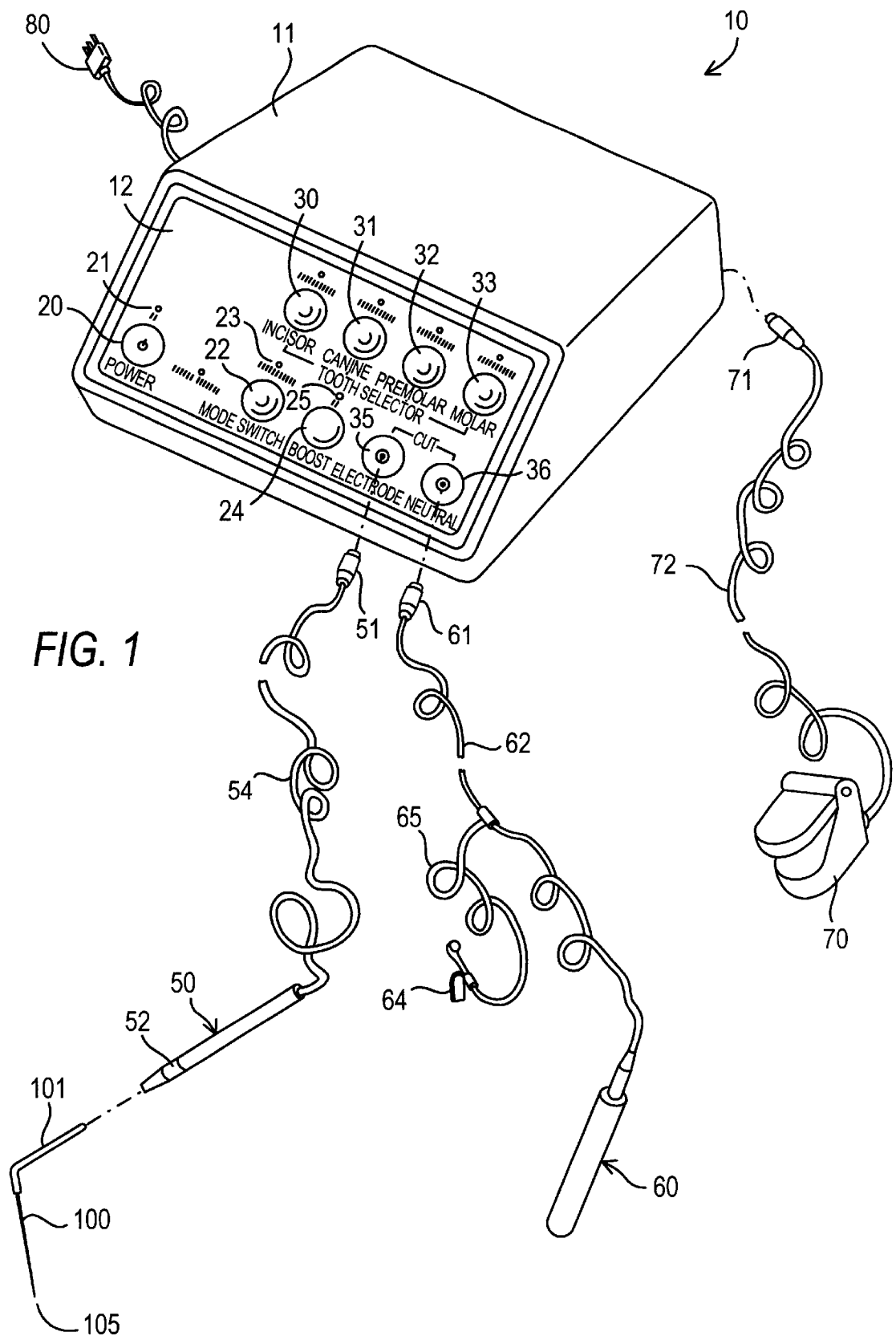

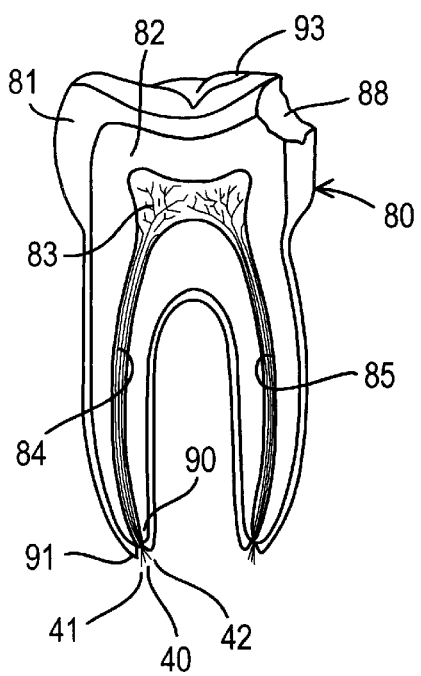
FIG. 2
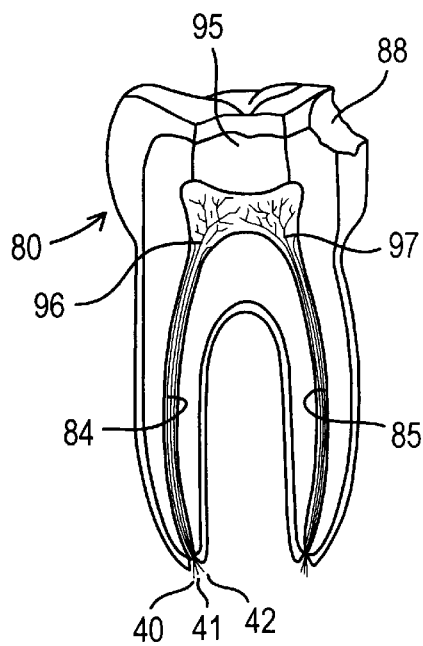
FIG. 3
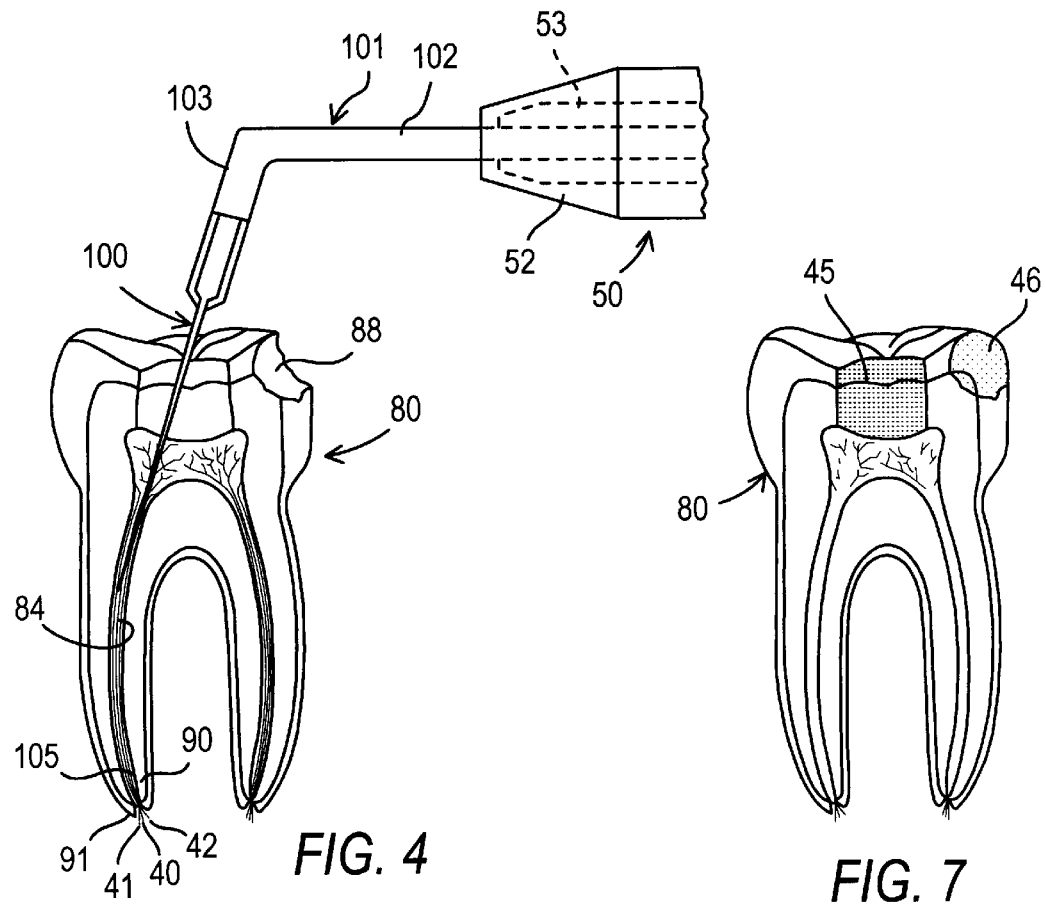
FIG. 4
FIG. 7

PROCESS FOR DEVITALIZING TEETH USING HIGH-FREQUENCY ELECTRIC CURRENT

The invention concerns medical equipment for dental use.

Before operating on a tooth to remove decay or for other purposes it is known that the vascular and nerve tissue inside the canal in the root of the tooth concerned has to be removed.

This is done by introducing into said canal an instrument which by lateral and rotary movements can bring to the surface the material inside it. There may be one or more canals according to the type of tooth. The operation may involve some considerable difficulty because of curves in canals and their divisions.

The instrument used for the purpose does not always achieve the desired results because of the above-mentioned anatomical characteristics. This operation is long and laborious.

It also requires repeated X-ray checks to see that the work is proceeding correctly. To ensure that the canal has been devitalized it is essential not only to clean it out but also to avoid penetrating beyond the lower end of each canal.

A certain distance, about mm 1.5, must be maintained from the apical foramen to avoid infection and bacterial complications generally. Bearing in mind that to devitalize the canal root is a dental treatment that requires great precision and careful attention, dealing correctly with the problems that arise using present methods must clearly depend on the dentist's ability.

SUMMARY OF THE INVENTION

The present invention eliminates the above drawbacks almost entirely both as regards the patient and the operator as will be explained below. Subject of the invention is a process to devitalize the canal root of a tooth in which the vascular nervous material receives a fractionally long high frequency electric pulse, power values, time and frequency, being adjusted to suit the type of tooth.

To carry out this procedure an electrode in the form of a needle is inserted into the canal in the root; the electrode is of a length that allows it to penetrate until it reaches the right distance from the apical foramen and is connected to a pulse-generating apparatus.

Emission of high frequency pulses can be assisted by electrically connecting the electronic circuit that generates them to some other part of the patient's body, the hand for example, by a so-called neutral handle-type metal object, or by some other suitable tool.

The effect of this high frequency pulse that acts only along the whole surface of the needle-type electrode, is to disintegrate the vascular nerve matter and simultaneously coagulate the part of the vascular bundle that is not destroyed, as well as to sterilize the root canal.

In order to insert the needle-type electrode into the root canal, anaesthetic is applied to the area of the tooth concerned which is then opened up till entry into the root canal is visible.

The high frequency electric pulse is preferably provided by an apparatus that comprises an electronic circuit able to estimate the correct distance from the apical foramen to which the needle must penetrate and to give an acoustic and visual warning as soon as that position is reached. In this way the operator can have suitable electric current generated for destroying the nerve bundle in the root canal when the needle has reached the above position.

Closure of the electric circuit is preferably pedal-operated.

Values of electric current suitable for destroying the nerve bundle in the root are automatically regulated by the electronic apparatus according to which of the four buttons is pressed, these being respectively for the four types of teeth: incisor, canine, premolar and molar Value of the electric current can be increased by pressing a button for this purpose placed on the apparatus.

The needle-type electrode, preferably of stainless steel, that transmits the high-frequency pulse, can be of different lengths, average mm 30, and may be of a tapering structure with a base diameter of about mm 0.25 and a tip diameter of about mm 0.1.

In a preferred execution the needle has a haft, about mm 1 in diameter, comprising a rear section about mm 15 long and a front section about mm 5 long set at an angle of about 110° in relation to the rear section.

The apparatus that actuates the described process comprises a cable for electric feed, a cable for pedal control of the devitalization pulse, a socket for a cable connecting it to a so-called active handle of insulating material with a metal core, and can comprise a socket for the cable connecting it to the so-called neutral handle.

At the front end of said active handle is a head into which the needle can be introduced and fixed.

The cable connected to the so-called neutral handle can include insertion of a branch cable to carry a kind of pincer which is preferably applied to the lip of the patient during the measuring operation.

The apparatus here concerned may be equipped with the following main electronic circuits: input filters, feeder, RF pulse generator or pulser, for setting output power, a power visualizer for setting Burst time, for the change-over from manual to automatic functioning or vice versa, for protection against an increase in the output power setting, for safety to prevent involuntary repetition of the devitalization movement before a set time, for example 10 seconds, has passed, for an acoustic two-tone warning when, during the measuring operation, the needle has penetrated to the correct distance from the apical foramen and for a single-tone sound to indicate that the devitalizing electric pulse has been given and that the operation has therefore been completed.

The process offers evident advantages.

Present mechanical methods involve a risk of bacteria remaining in the canal of the root that may lead to pathological conditions of the tooth or of its adjacent structure producing haemorrhage or infection.

The method described makes it possible to devitalize the root canal quickly and painlessly using very little anaesthetic which is therefore less toxic for the patient.

After the operation the root canal is completely sterilized both in its main part and in its lateral branches.

Any haemorrhage or infections are entirely avoided.

The risk is also avoided of penetrating beyond the apical formen, a risk always present with the manual instruments in use, and one that can lead to considerable complications.

To sum up these advantages, with a small low-cost easily operated apparatus, for the first time in the field of dentistry apical measurement and electronic devitalization can be done limiting the operation exclusively to disintegration of the vascular nerve bundle.

In conclusion, this method enables both dentists and patients to undertake dental treatment in an entirely new way which offers important advantages, not only in time and cost but also in patient comfort, maximum reliability and elimination of errors.

Characteristics and purposes of the invention will be made still clearer by the following example of its execution illustrated with diagrammatically drawn figures.

FIG. 1 Perspective view from above of the apparatus used to execute the invented process.

FIG. 2 Longitudinal section of a decayed molar tooth.

FIG. 3 The tooth in FIG. 2 after opening it for access to entry to the root canal.

FIG. 4 The tooth during measurement of depth of the root canal.

Figure 5:
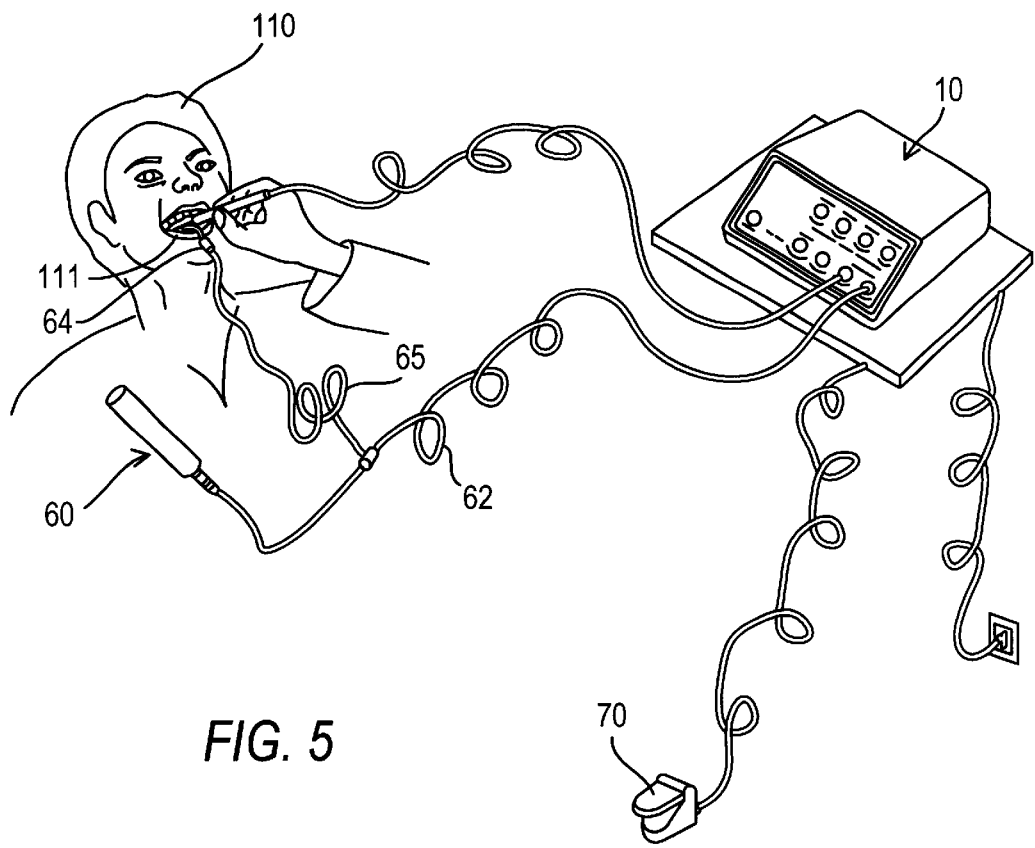

FIG. 5 The patient during measurement of depth of the root canal.

Figure 6:
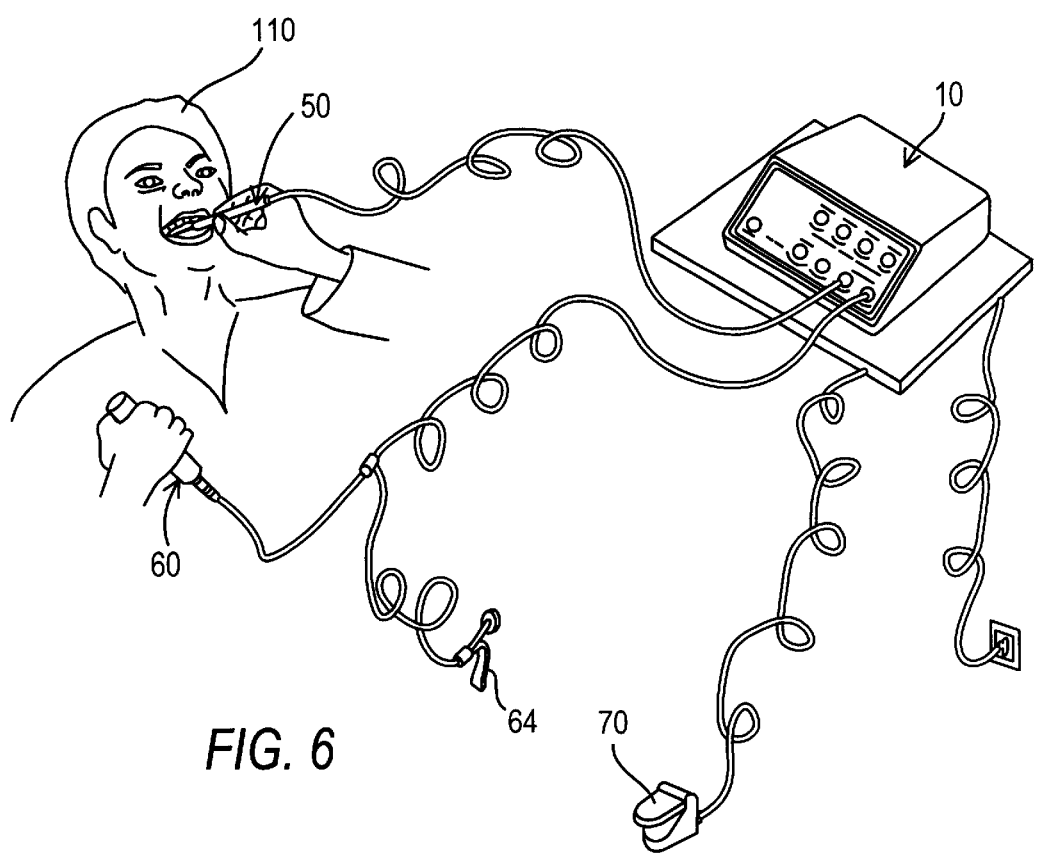

FIG. 6 The patient during the process of devitalizing the root canal.

FIG. 7 The tooth in FIG. 2 after devitalization and the canal closed.

Figure 8:
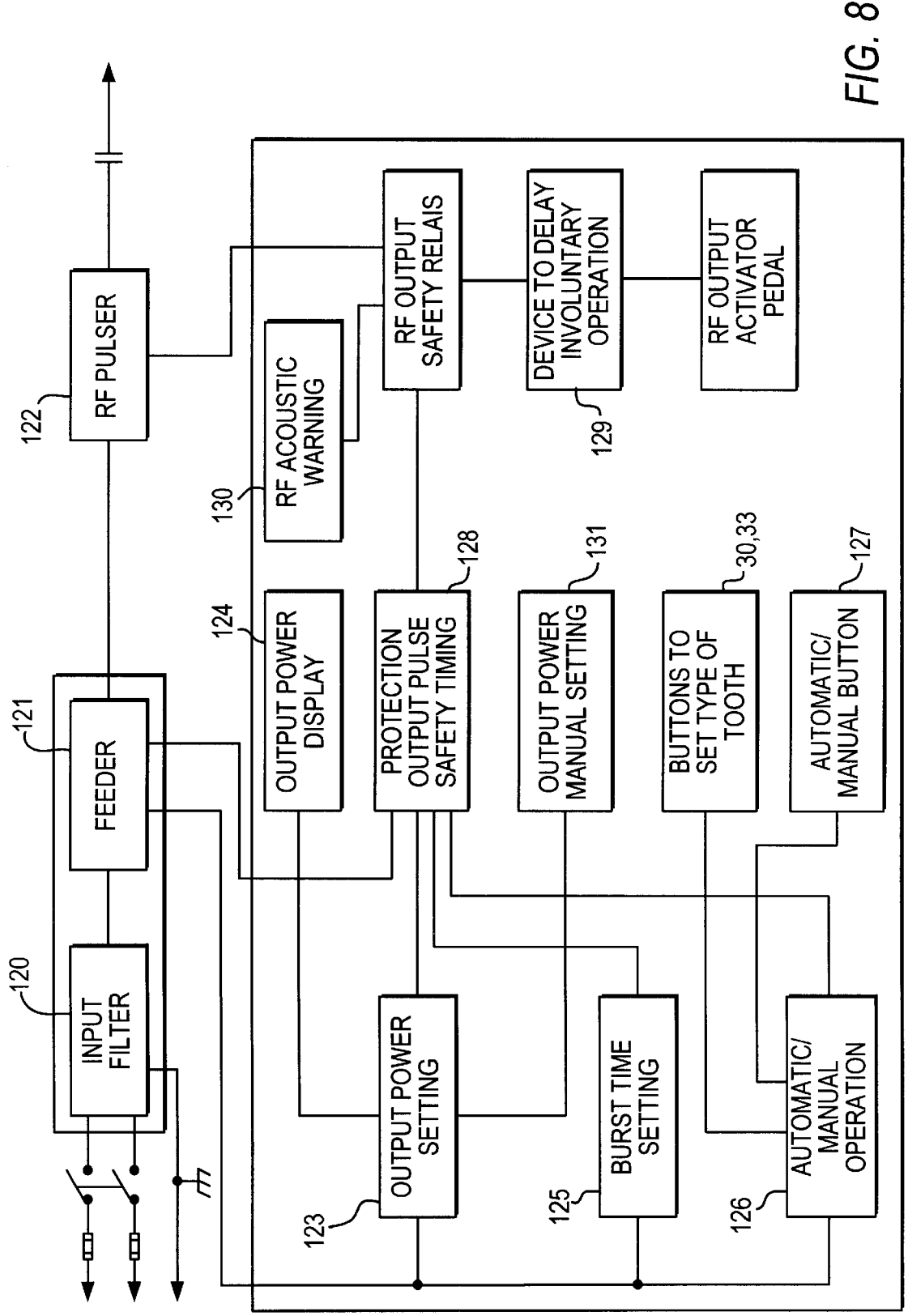

FIG. 8 Electronic diagram of the apparatus.

Figure 9:
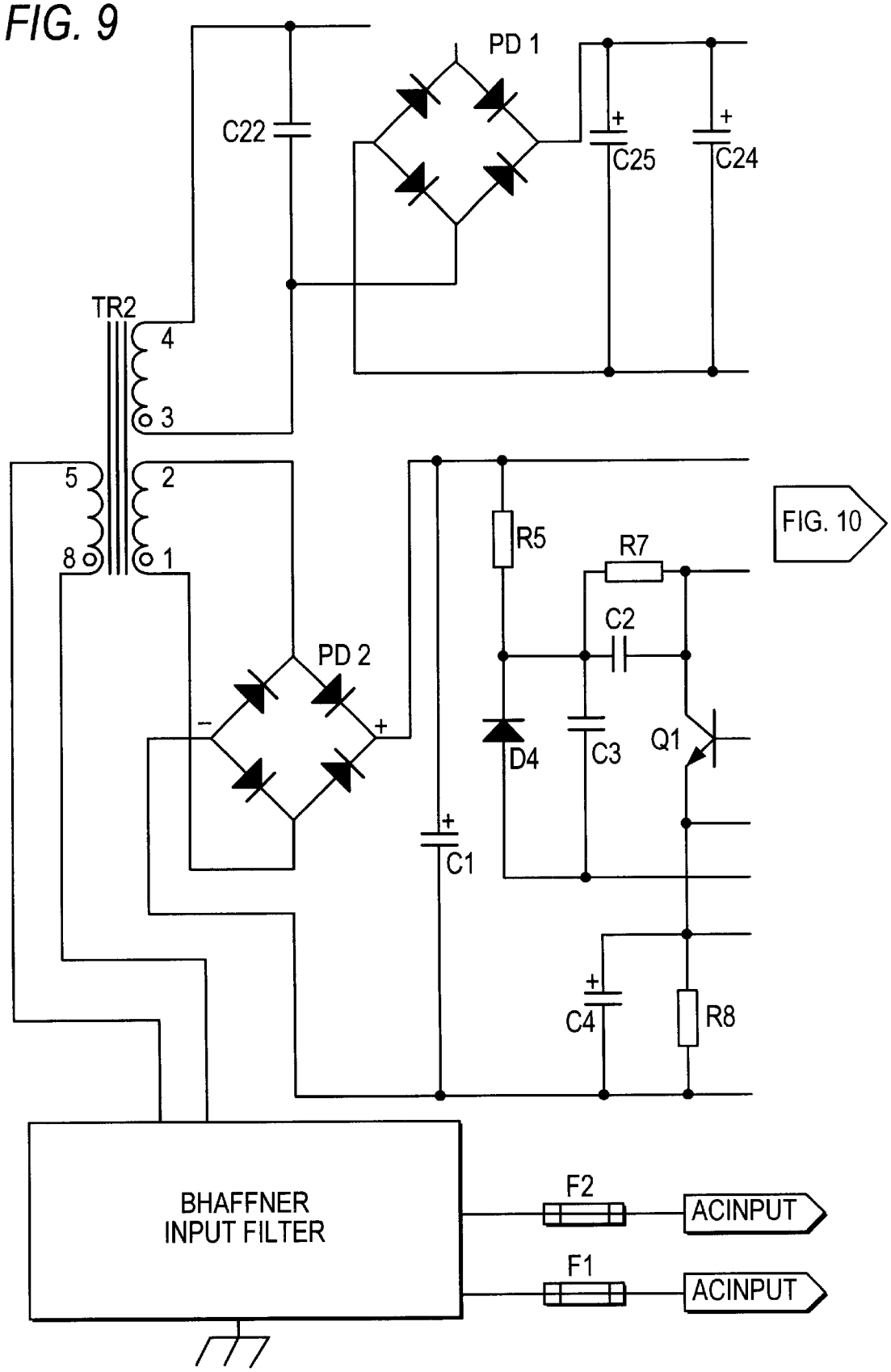
Figure 10:
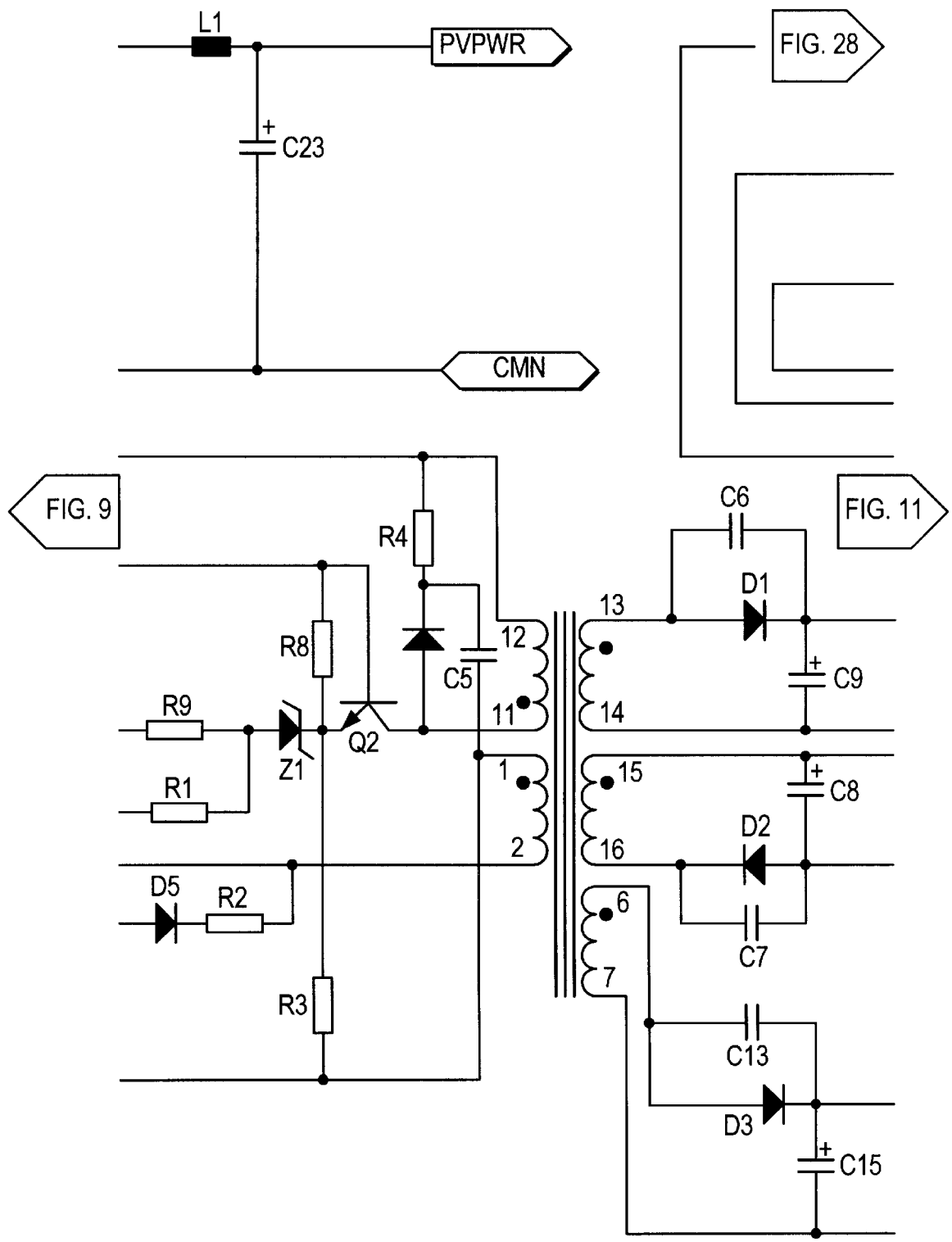
Figure 11:
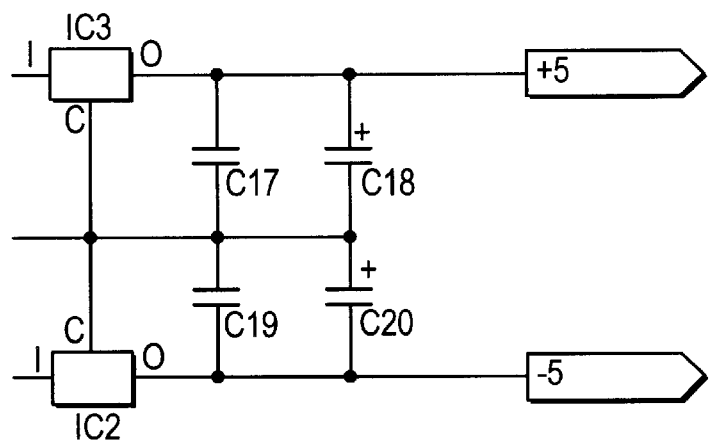
Figure 11:
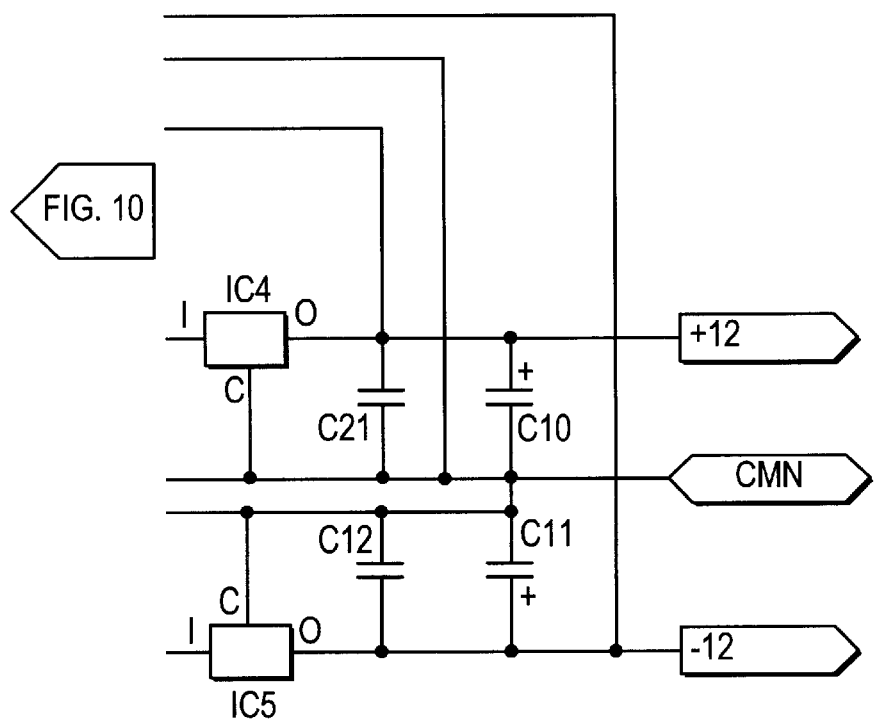
Figure 11:
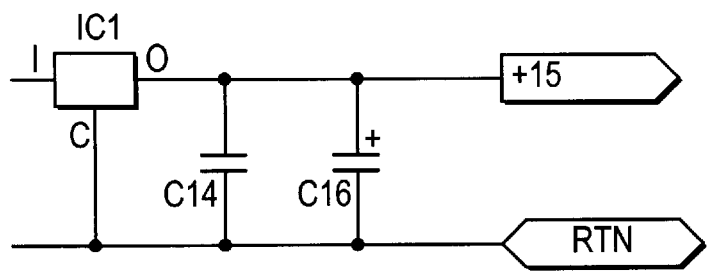

FIGS. 9–11 Electronic diagram of the feeder

Figure 12:
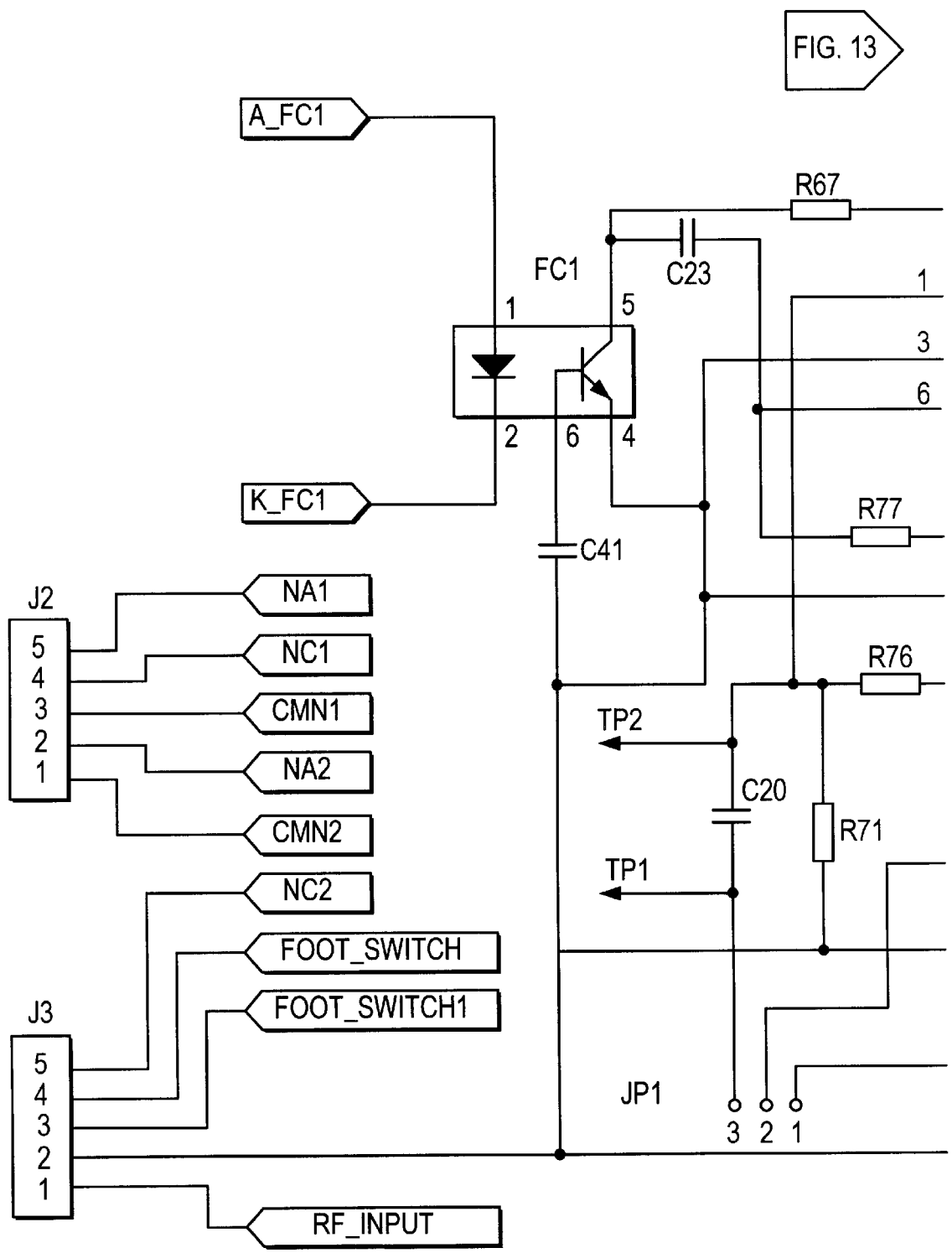
Figure 13:
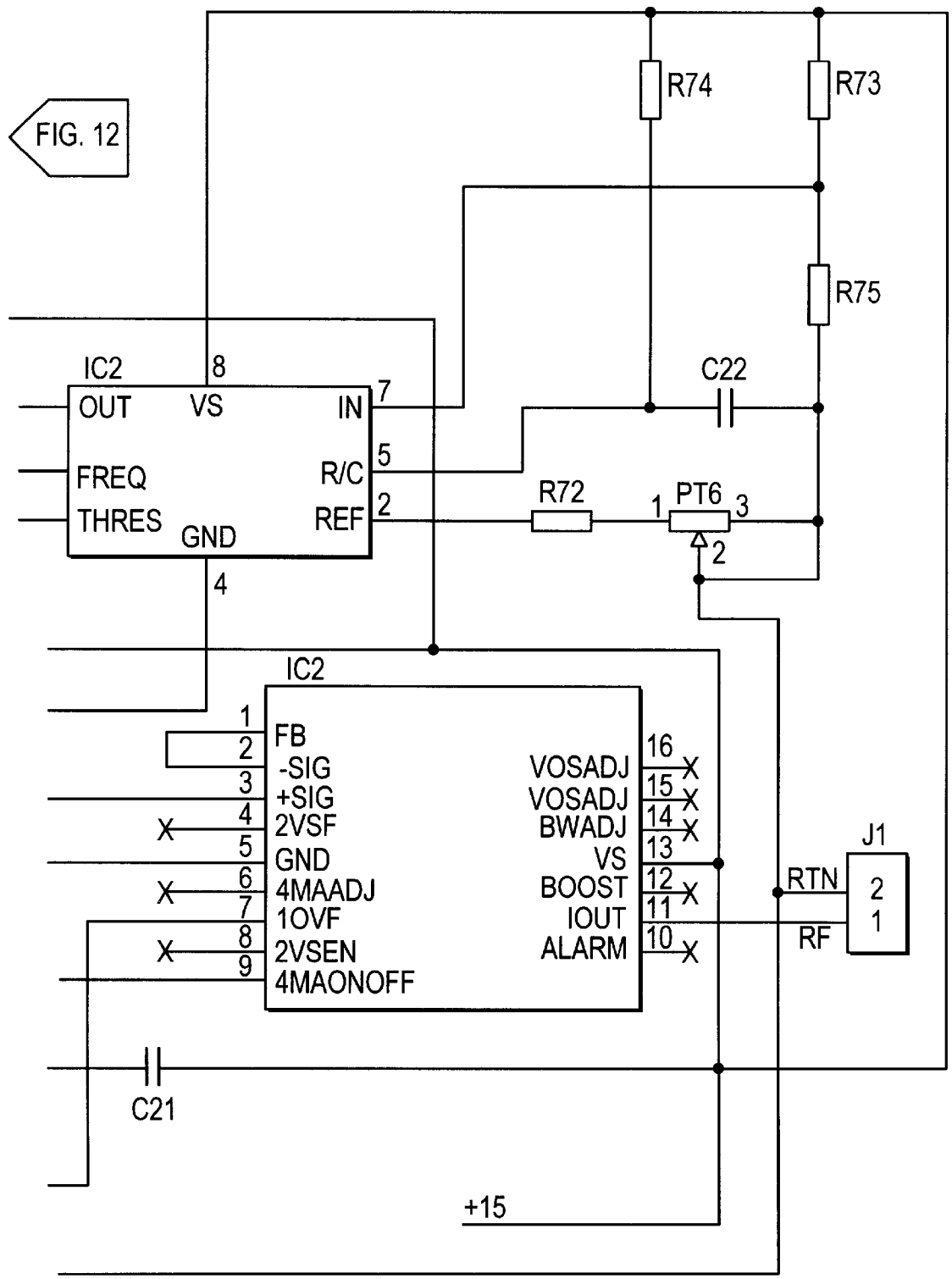
Figure 14:
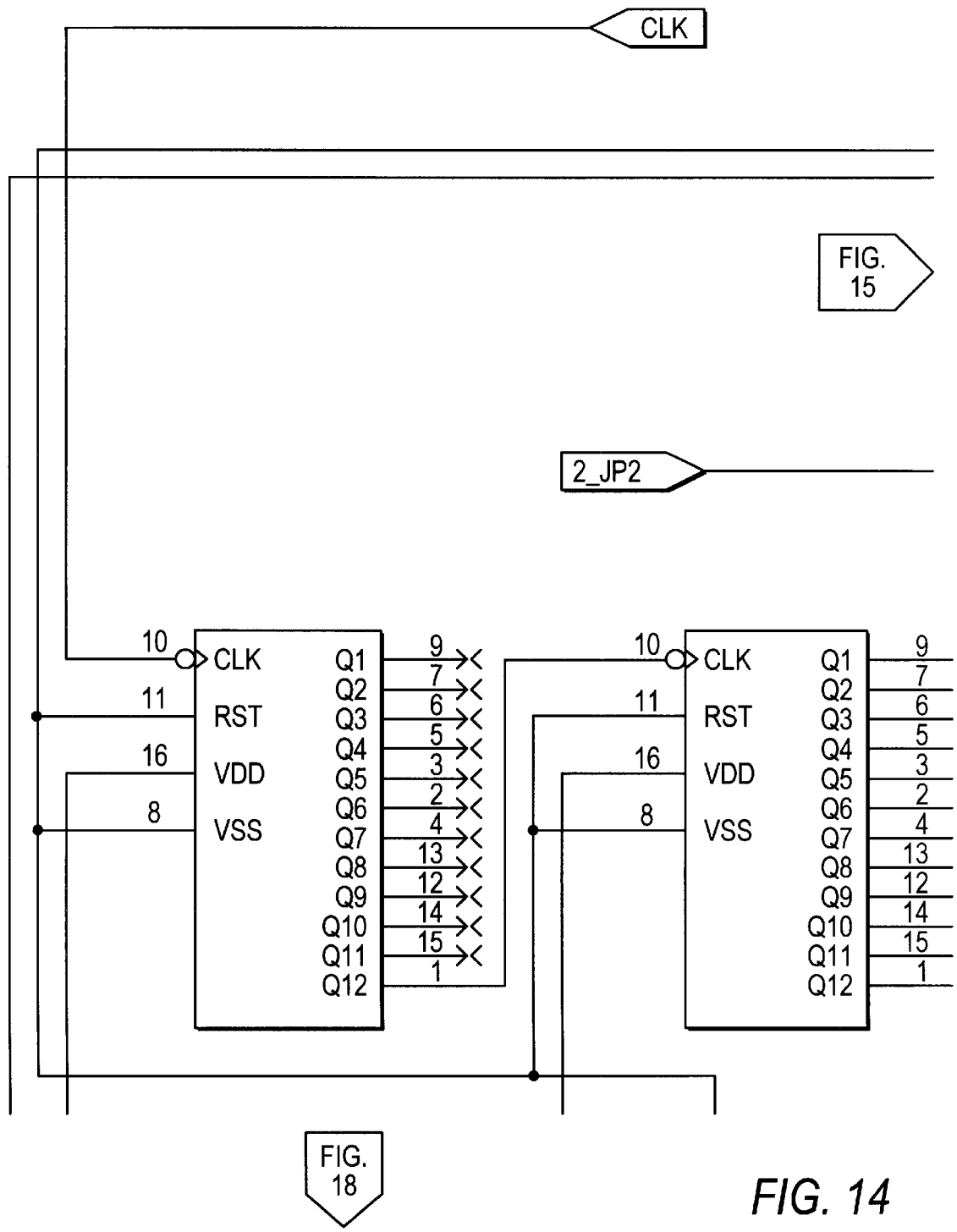
Figure 15:
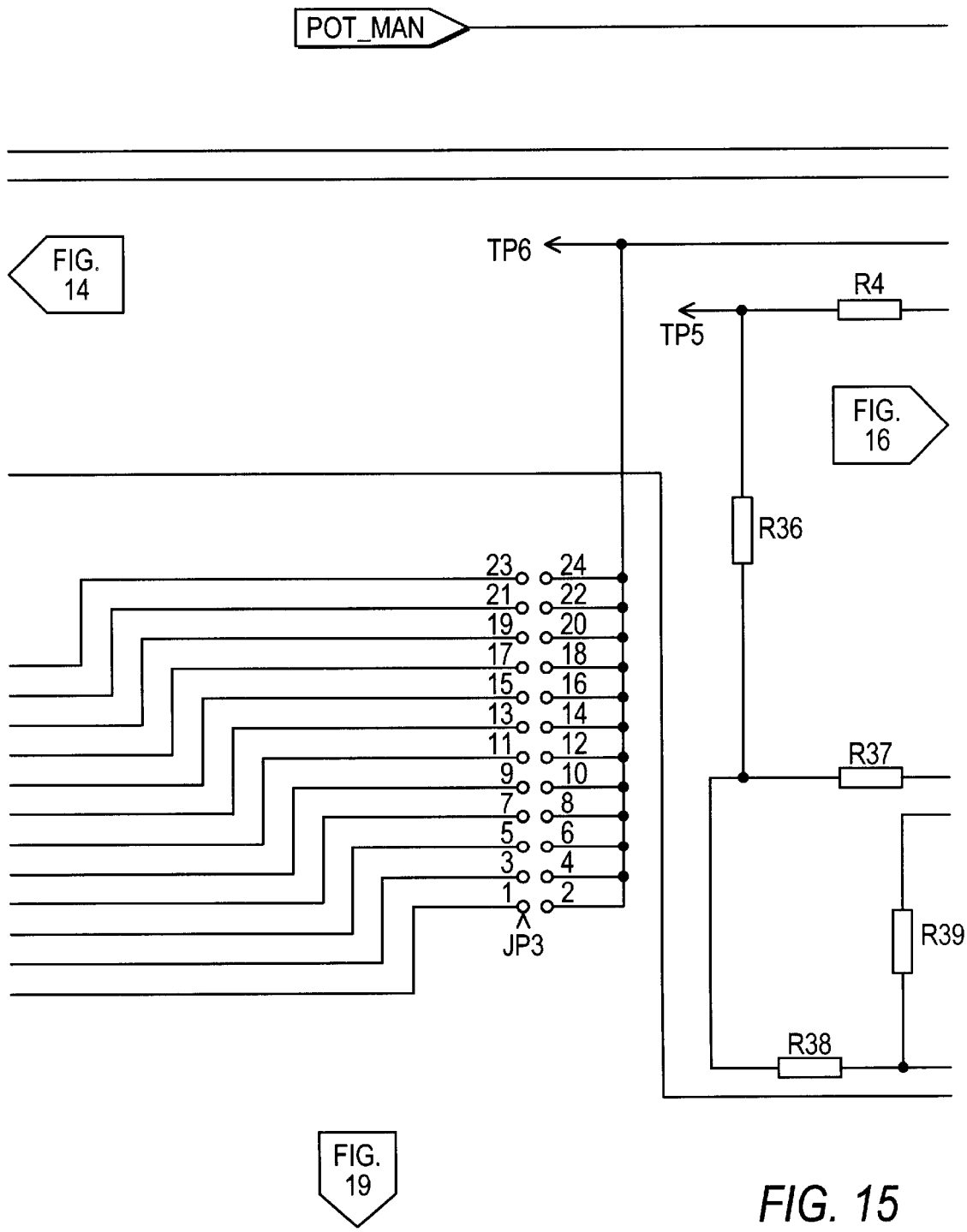
Figure 16:
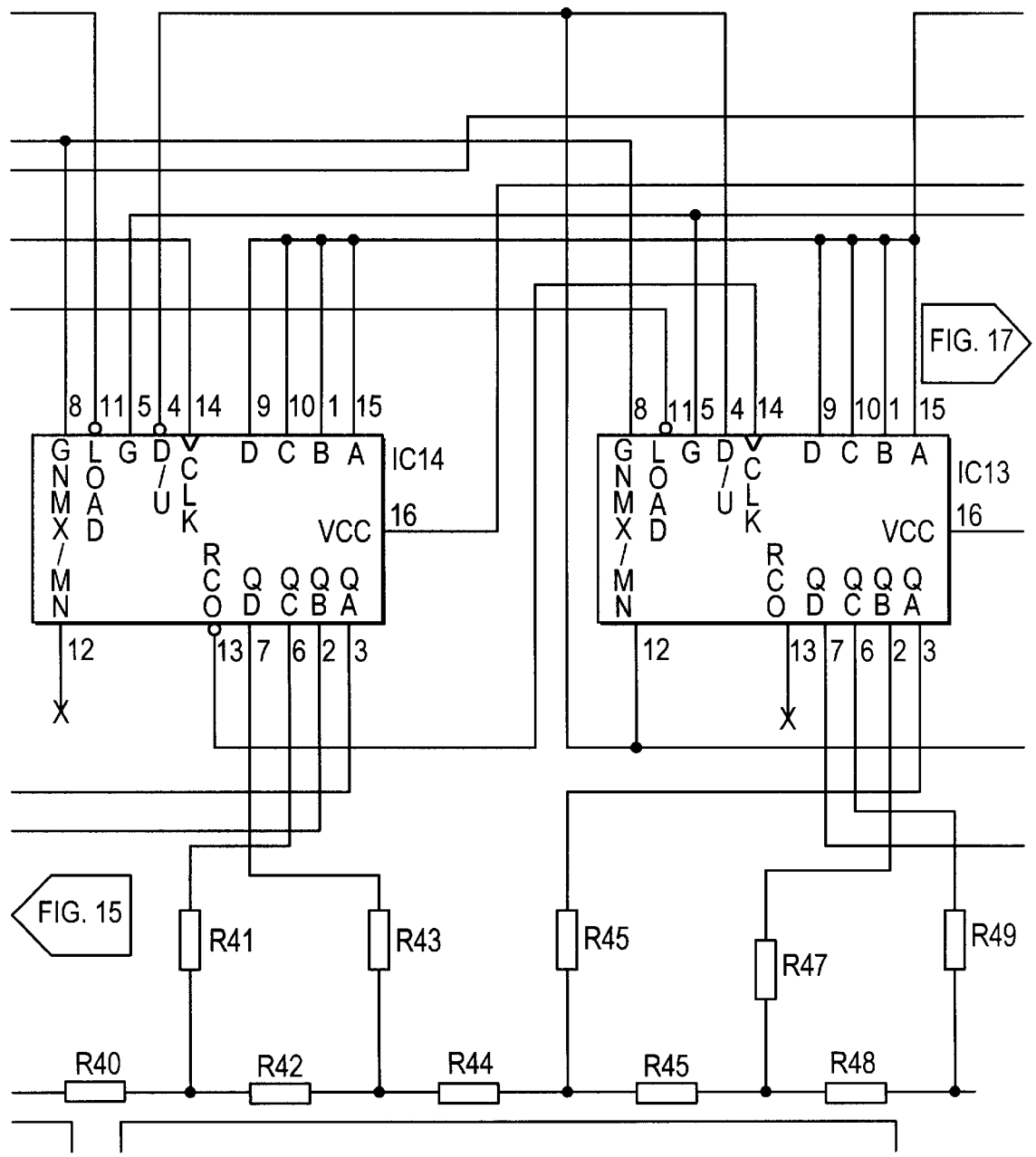
Figure 17:
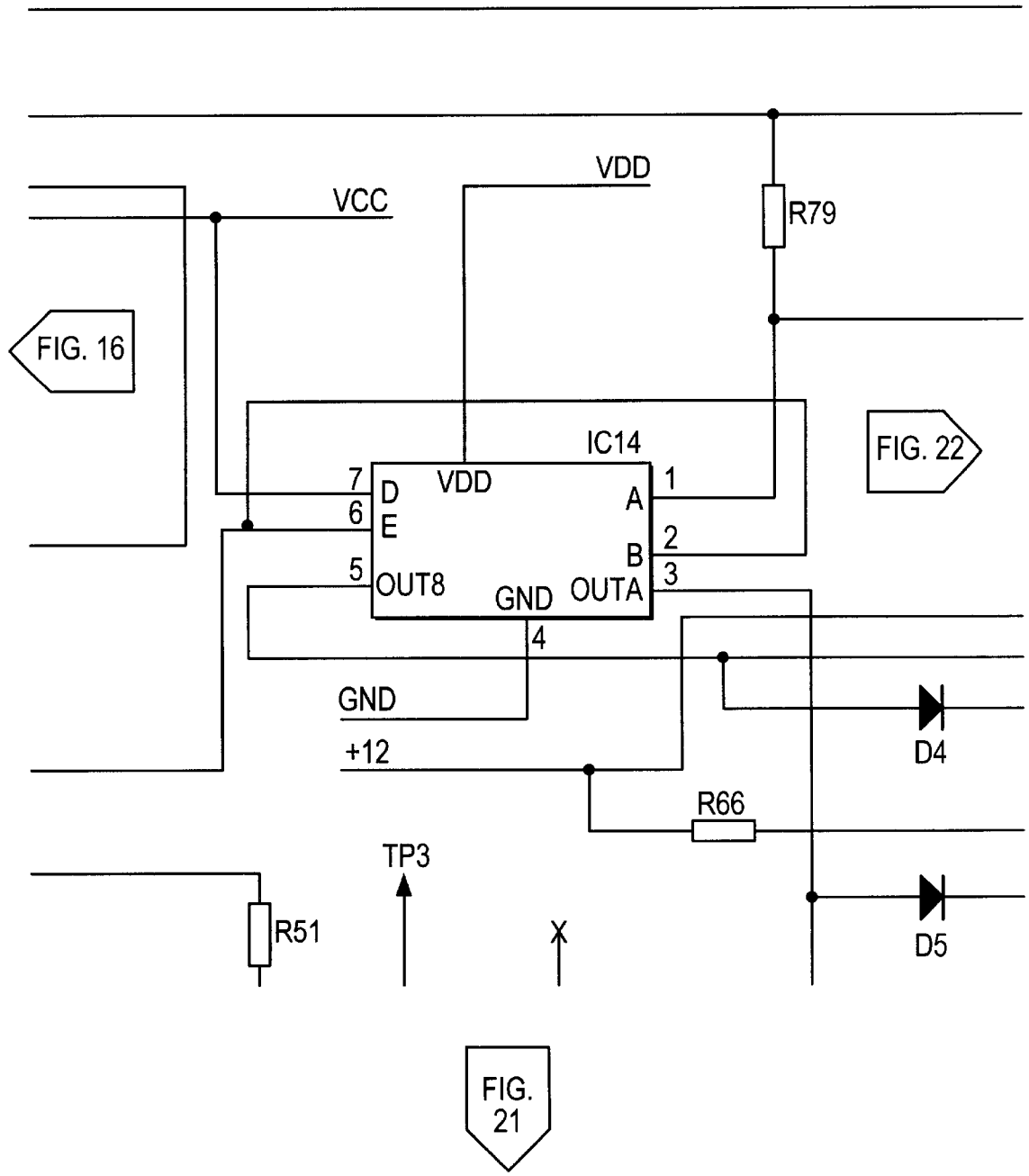
Figure 18:
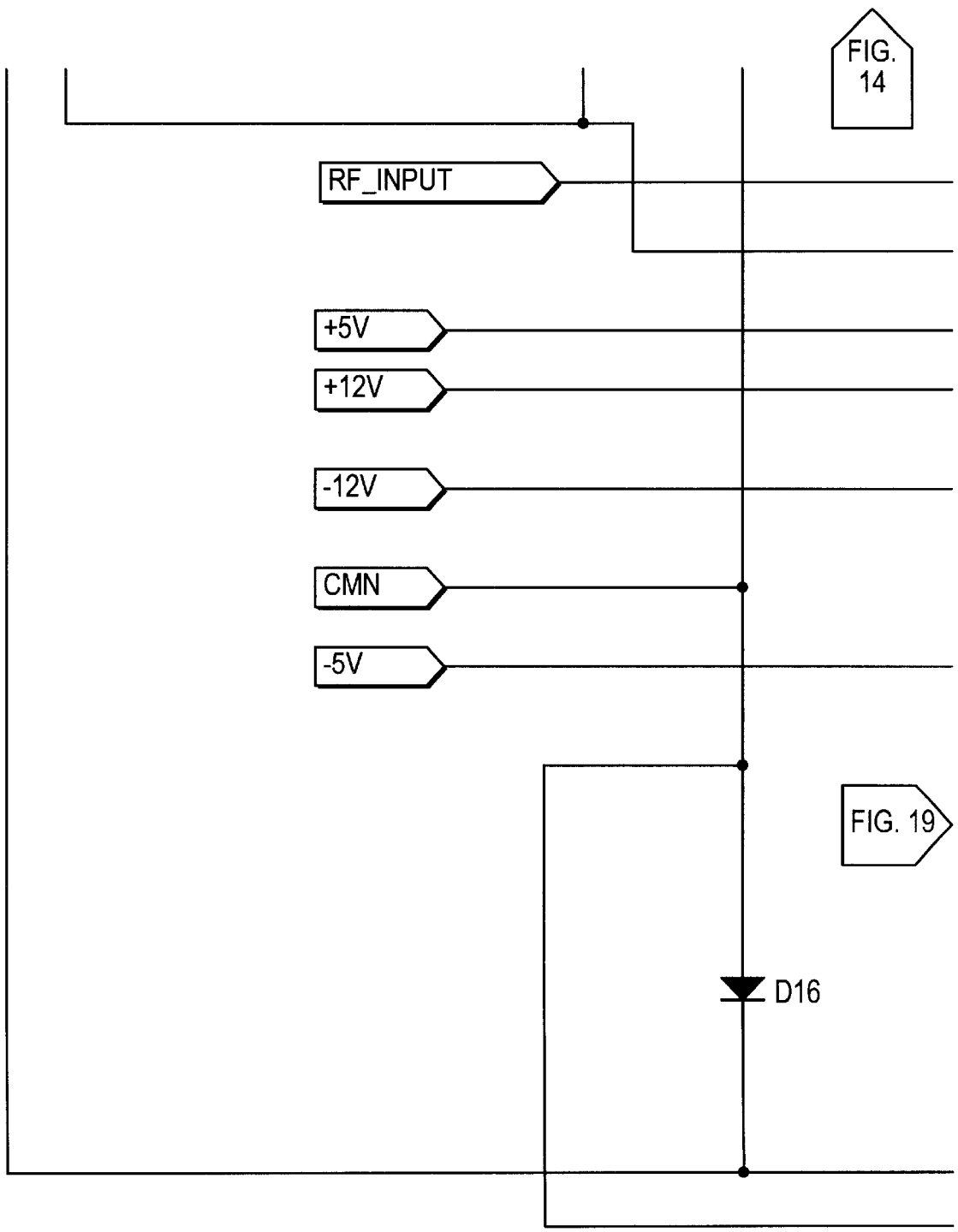
Figure 19:
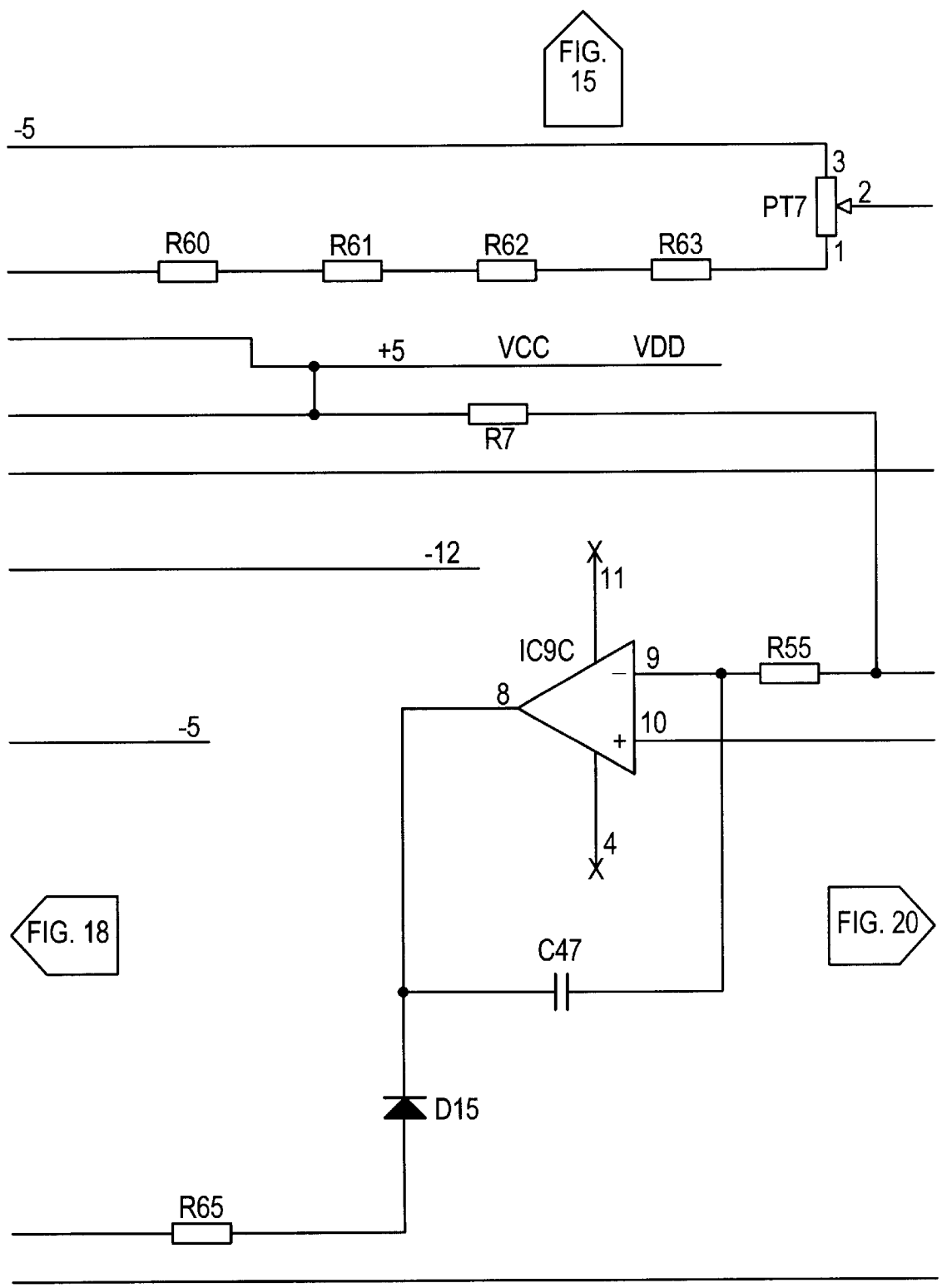
Figure 20:
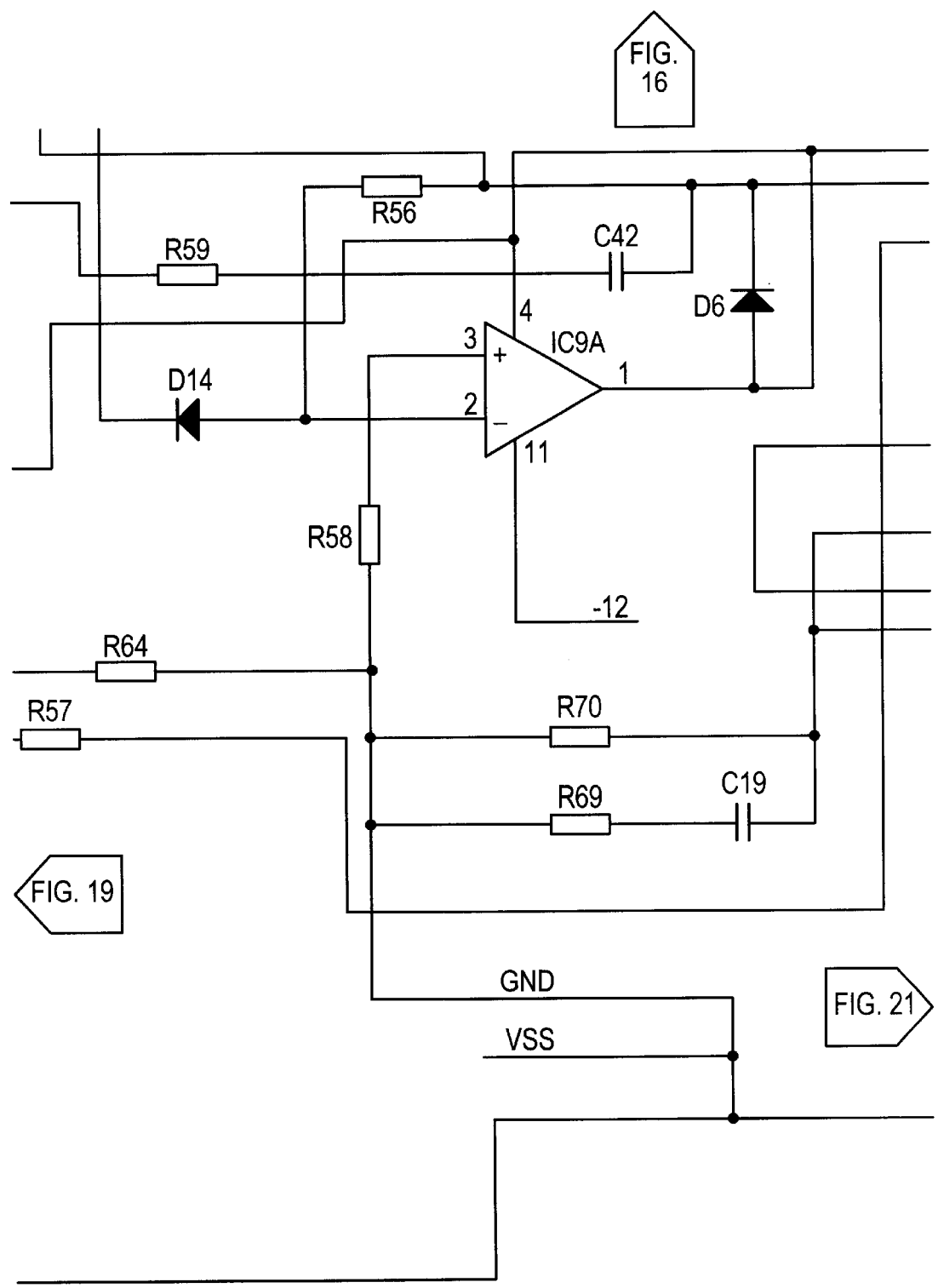
Figure 21:
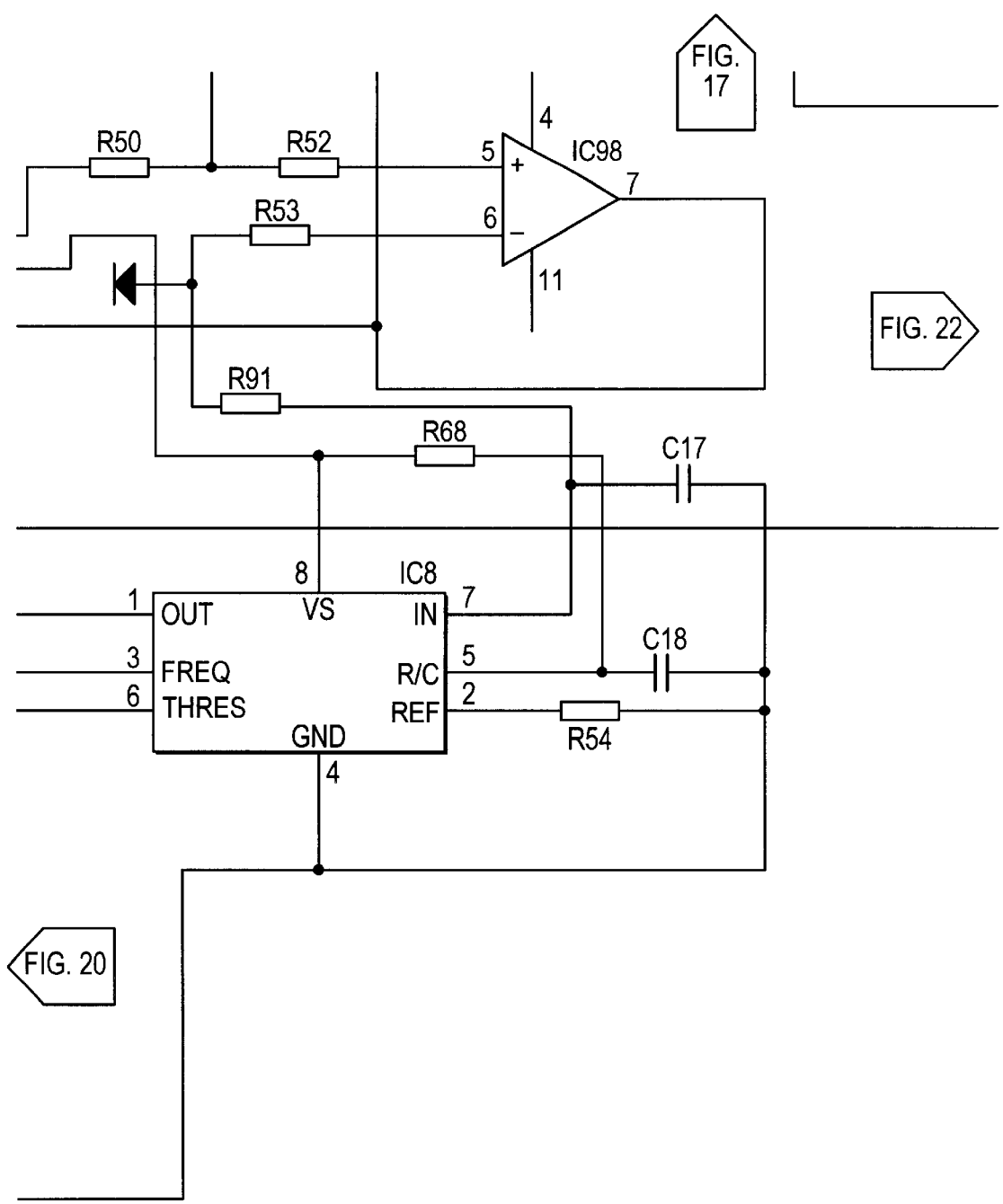
Figure 22:
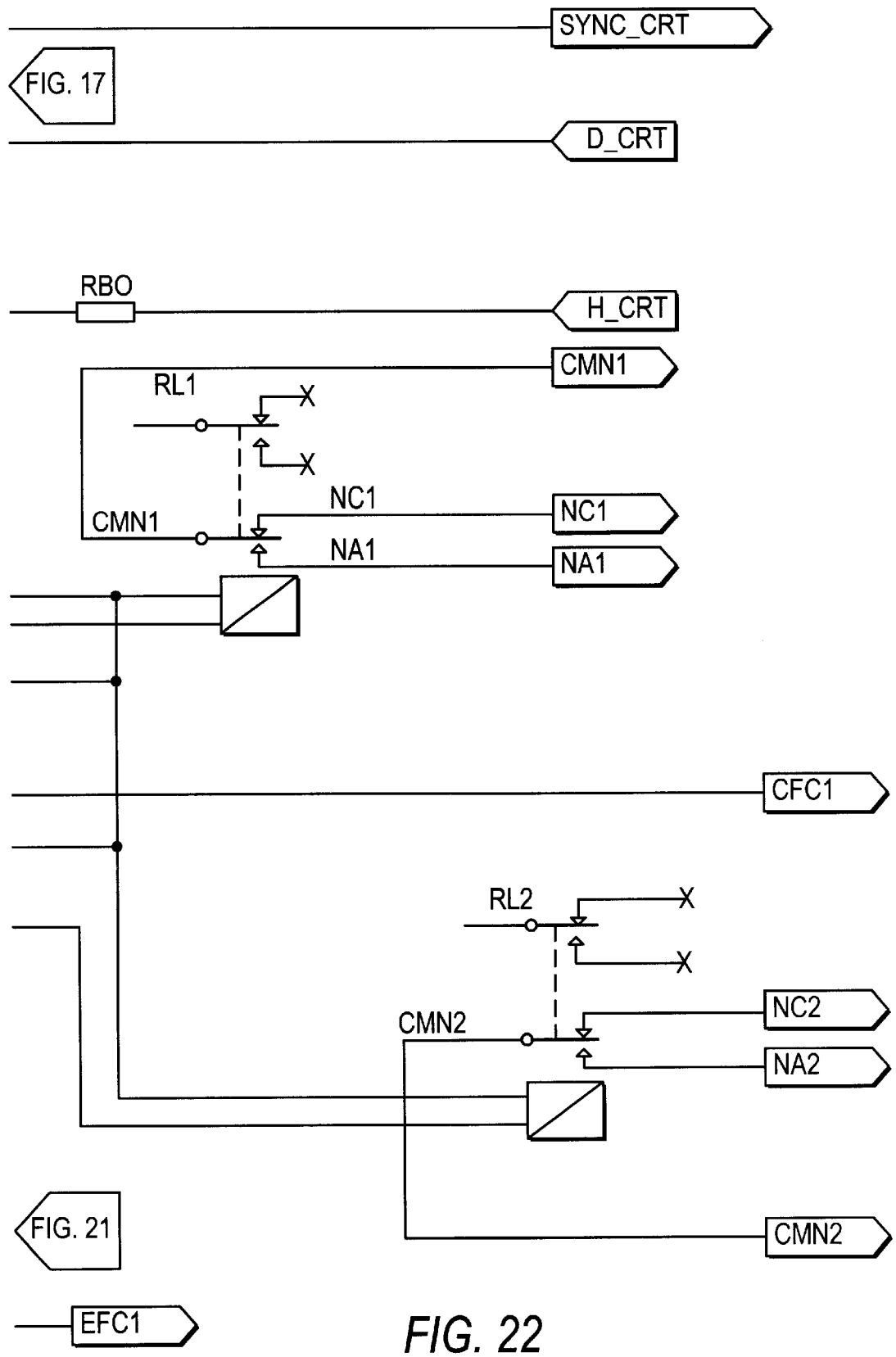

FIGS. 12–13 Electronic diagram of RF output and controls.

FIGS. 14–22 Electronic diagram of time selection and CLK.

Figure 23:
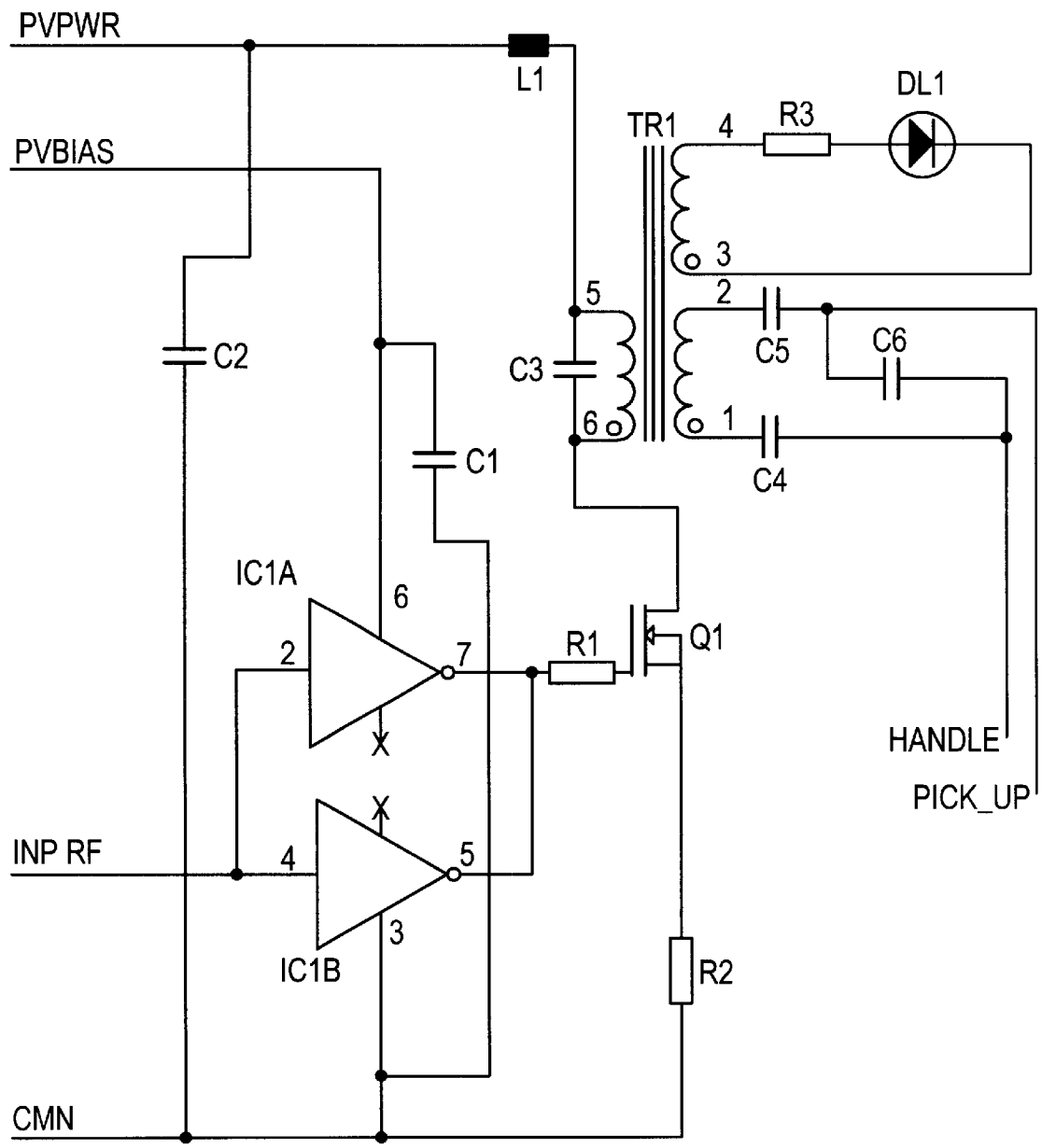

FIG. 23 Electronic diagram of the RF power pulser.

Figure 24:
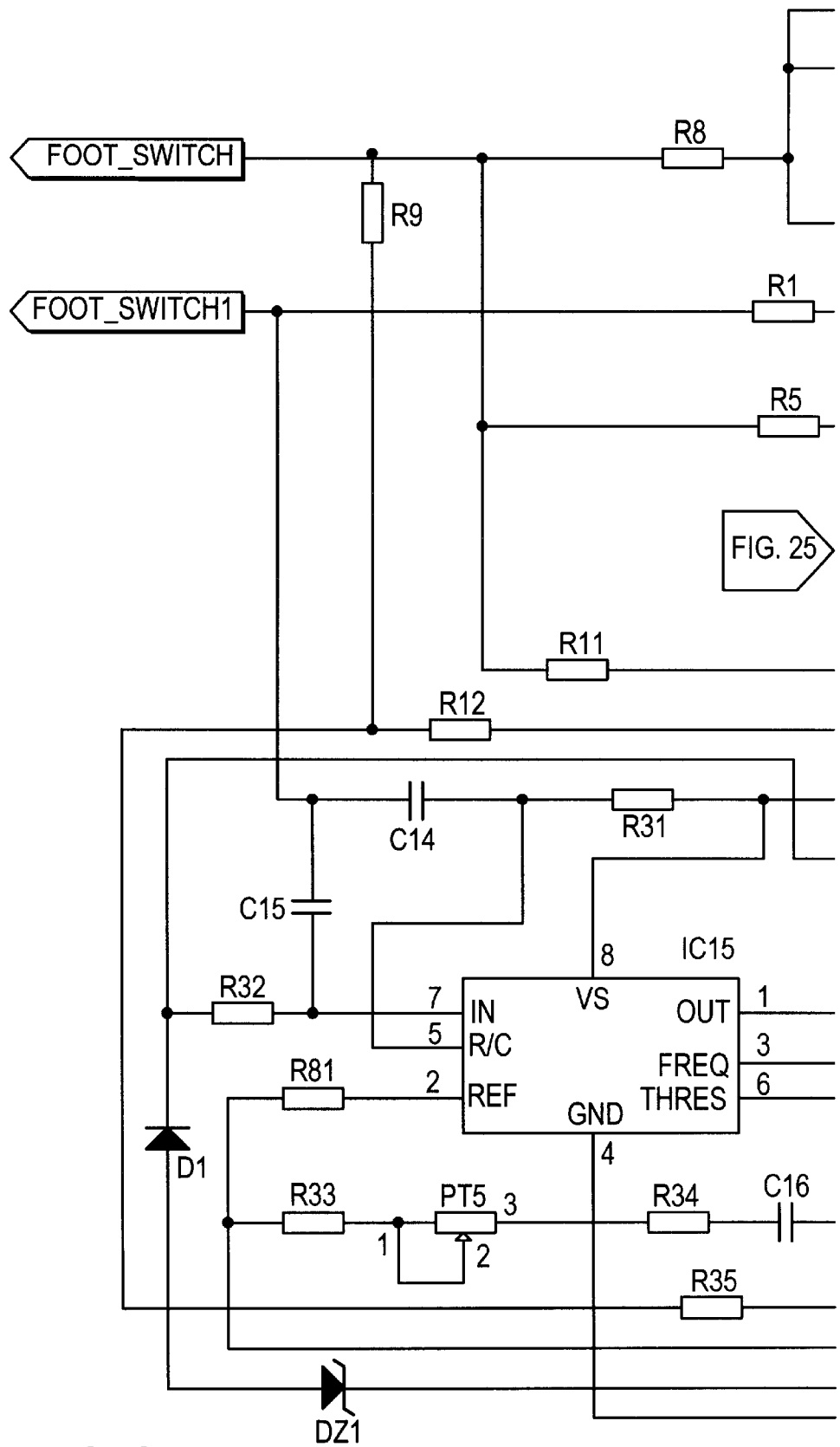
Figure 25:
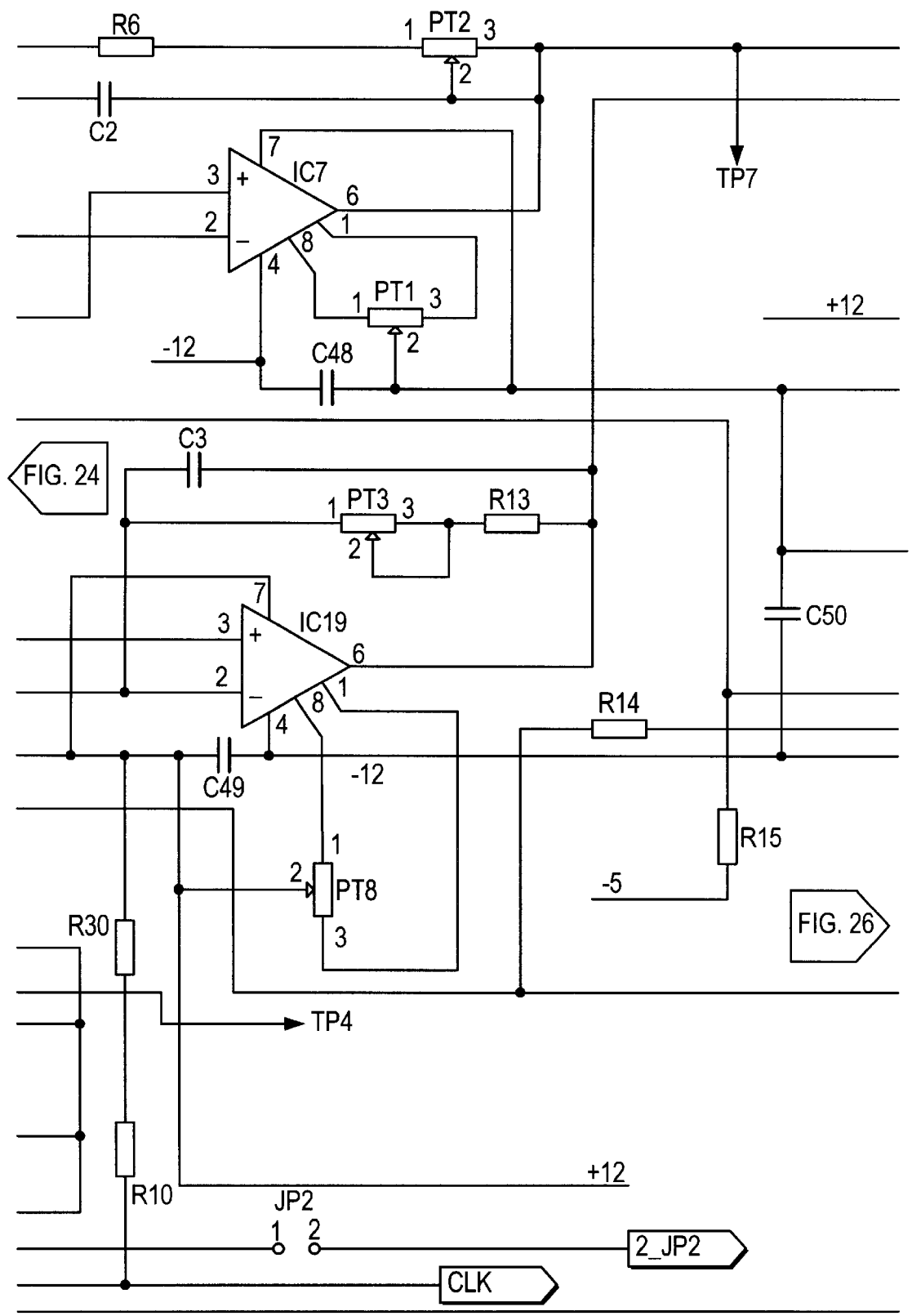
Figure 26:
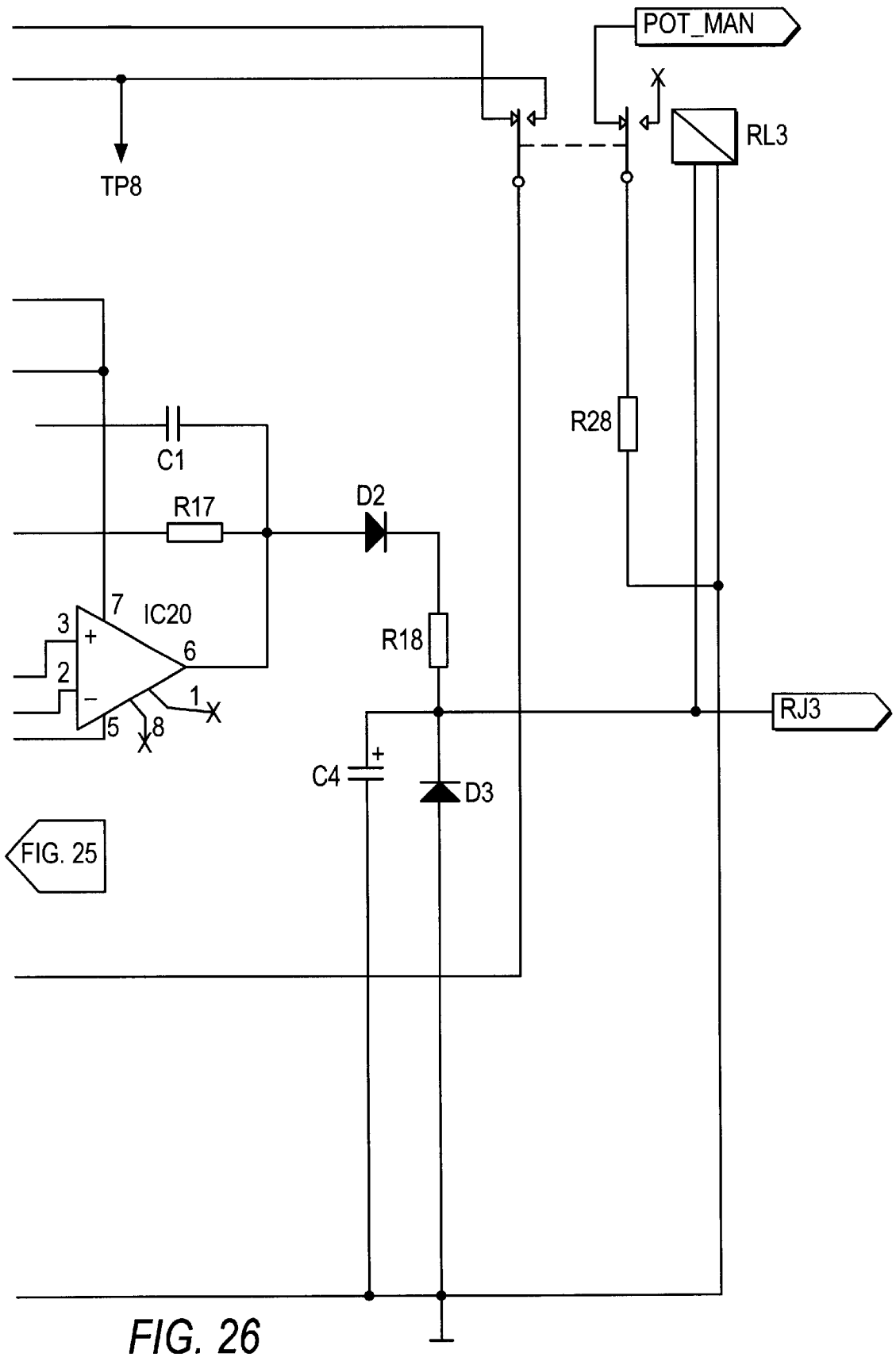

FIGS. 24–26 Electronic diagram of RF output power regulation.

Figure 27:
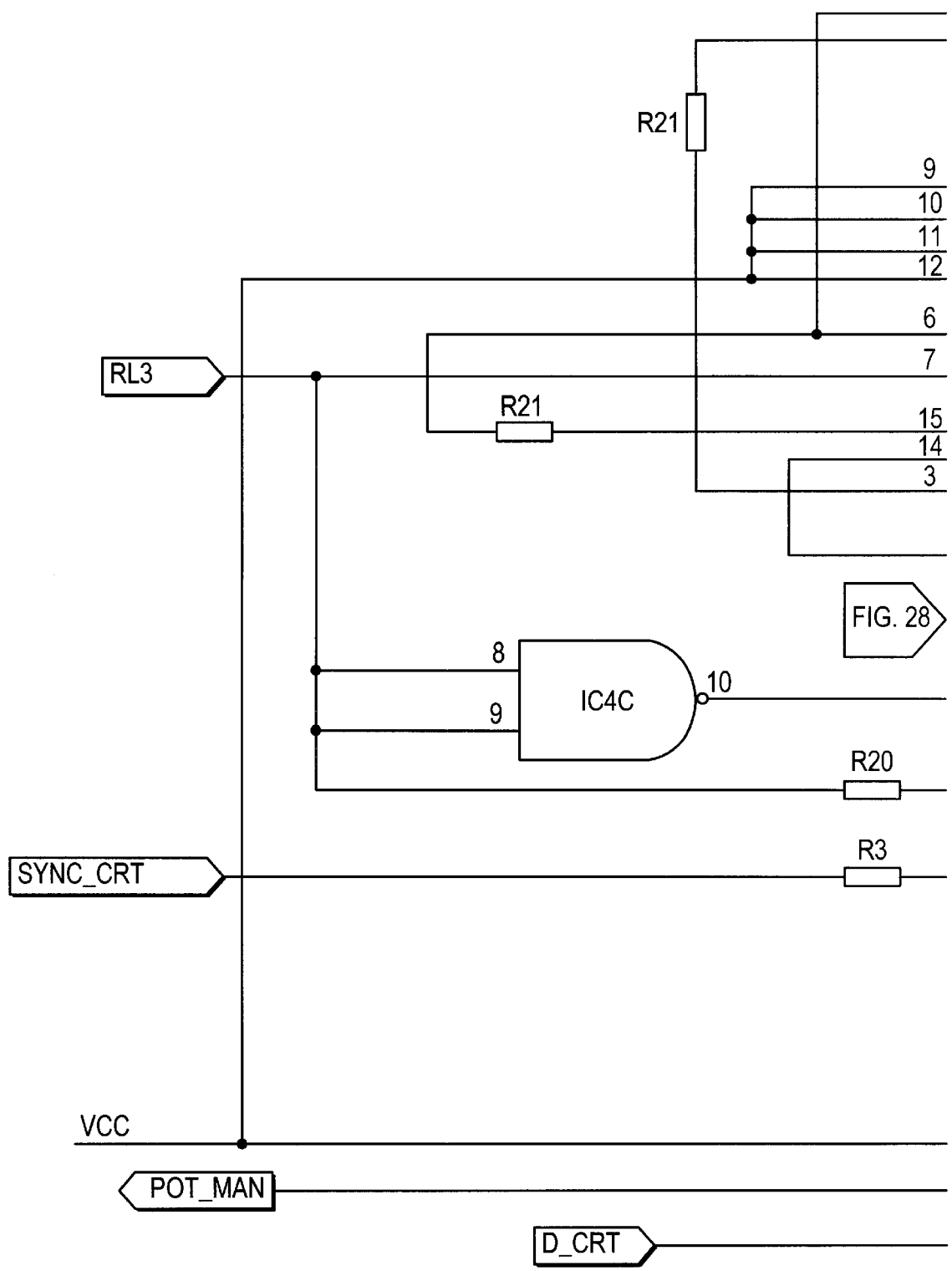
Figure 28:
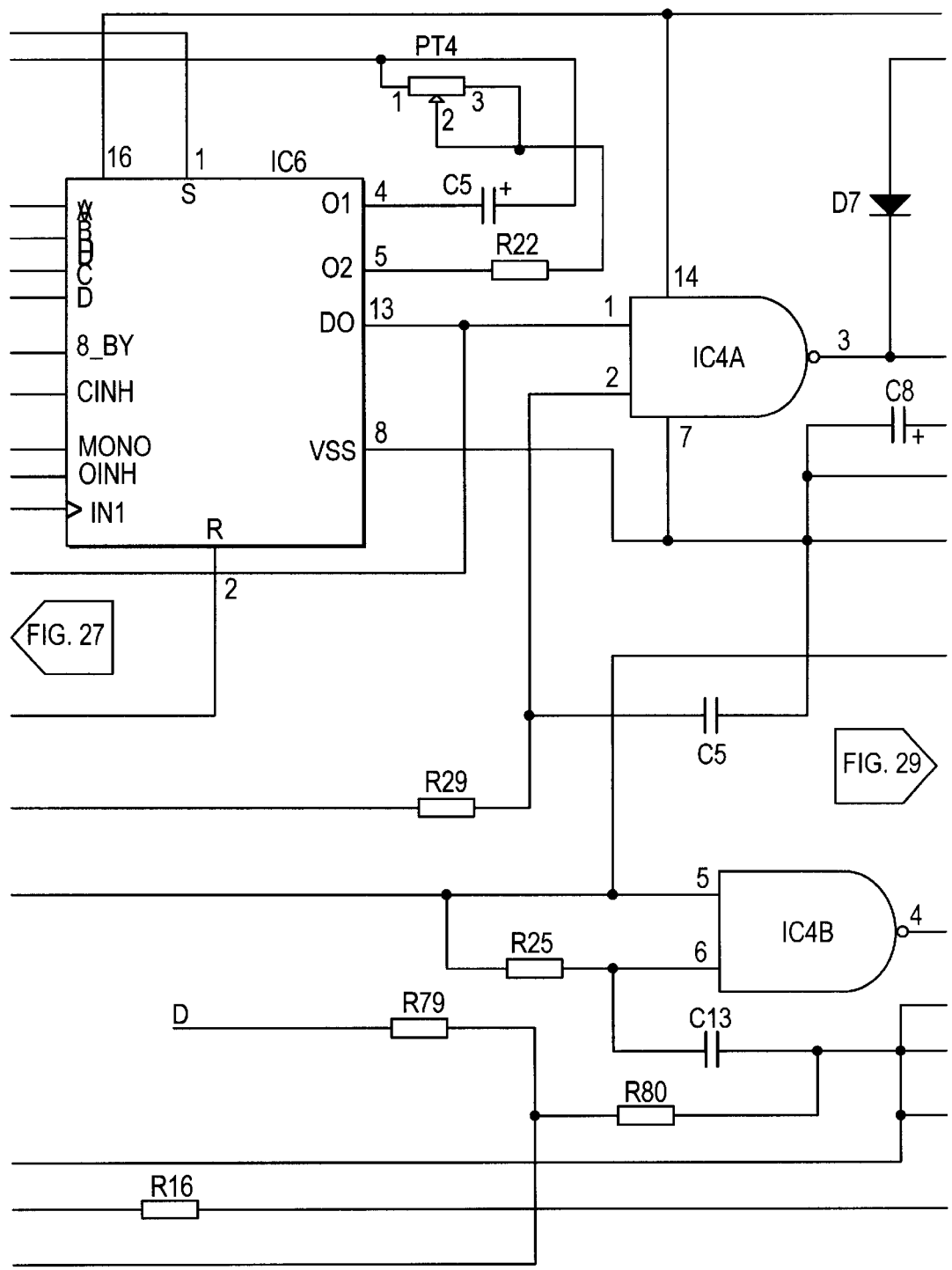
Figure 29:
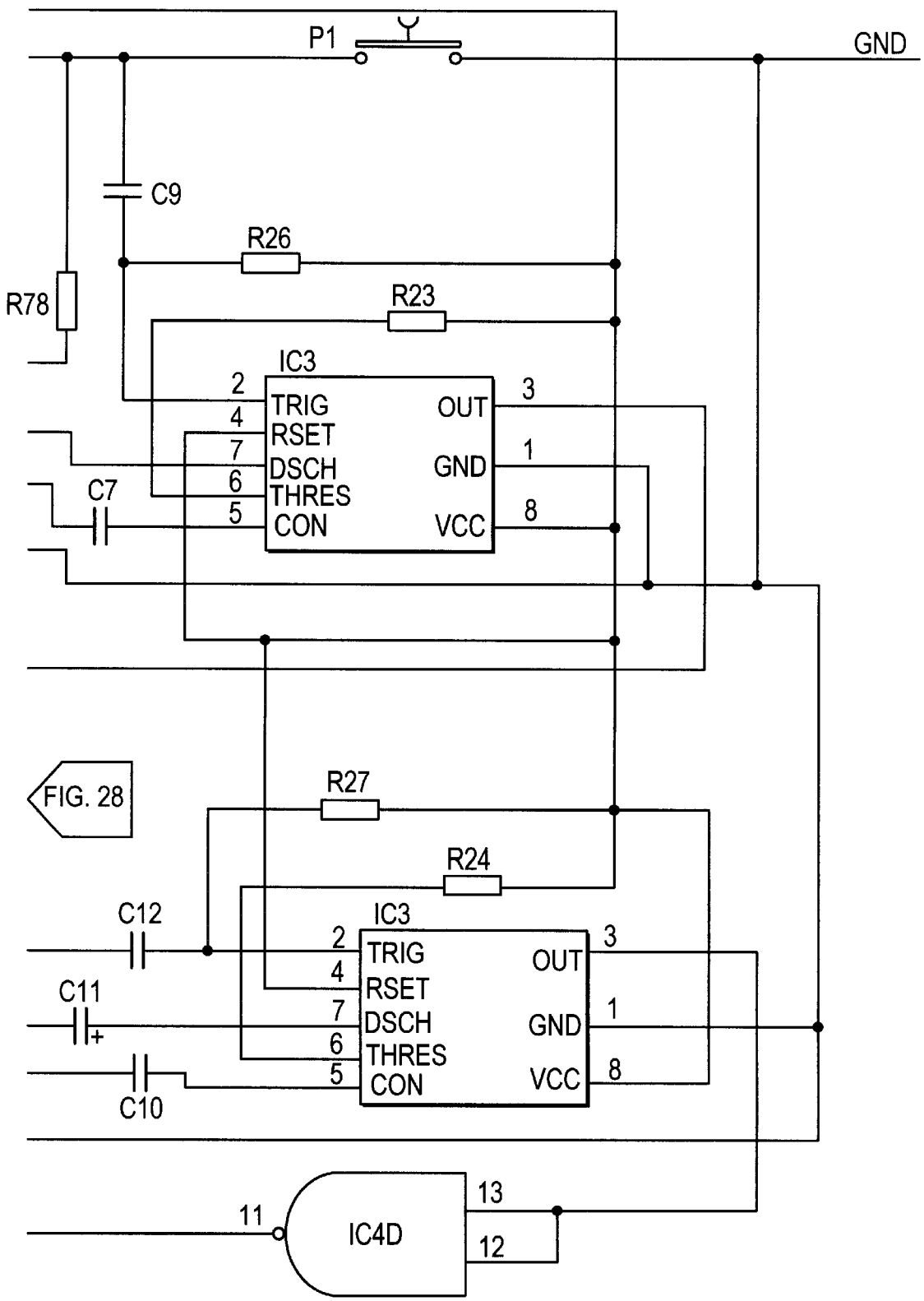

FIGS. 27–29 Device for delaying involuntary movements.

DESCRIPTION OF THE PREFERRED EMBODIMENTS

The apparatus 10 comprises a substantially parallelepiped box 11, flat with a front 12 inclined at about 45°.

Approximate dimensions of this box are mm 250×250×100.

The following controls are placed on the front of the box:

Push button 20 with pilot light 21 for turning the apparatus on and off.

Push botton 22 with pilot light 23 for passing to the measuring "mode".

Push button 24 with pilot light 25 for manual increase of power of the electric pulse.

Using the respective push buttons 30, 31, 32, 33, each with pilot light, the apparatus can operate suitable functional characteristics for the different types of teeth: incisor, canine, premolar, molar.

Sockets 35 and 36 receive the plugs 51 and 61 respectively for the active handle 50 and the neutral handle 60.

At the back of the apparatus, not seen in FIG. 1, there is a socket for plug 71 for working the pedal 70.

Electric feed is supplied through the plug 80. The active handle 50 is made of insulating material and includes an electrically conducting metal core 53 for contact with the metal needles. Said metal core is connected internally to the plug 51 through the wire 54.

Length of said handle is substantially mm 100, with a diameter of mm 12 in the head 52 into which can be inserted the haft 101 of the needle 100 as seen in FIG. 4

An assortment of needles is provided comprising various lengths, but the average length is about mm 30.

Their shape is tapered, diameter varying from about mm 0.25 at the base to about mm 0.1 at the tip (FIG. 4).

The needles are made of stainless steel.

Diameter of the haft 101 for the needles is about mm 1, length of the rear section 102 being about mm 15 and that of the front section 103 about mm 5.

The fore end is bent at an angle of about 110° compared with the rear. The active handle can be assisted by electric connection to the electronic circuit, that generates the high frequency pulses, with another part of the patient's body, the hand for example, by means of a so-called neutral handle 60.

Length of said neutral handle is about mm 100, diameter about mm 25; it is made of electrically conducting metal and is connected by the cable 62 to the plug 61.

There is a branch line 65 from said cable 62 to connect with an electrically conducting pincer 64 that can be fixed to a sensitive part of the human body, especially to the lip.

By means of the pedal 70 and electric cable 72 that connects to the plug 71, the devitalizing electric pulse can be controlled by the foot. To devitalize the root canal properly, it is necessary to penetrate close to the apical point but to avoid going beyond it.

FIGS. 2 and 3 show in perspective, a cross section of a premolar 80 with its crown 81, dentine 82, pulp 83, root canals 84, 85, bundle of nerves 40, artery 41 and vein 42.

These canals have an anatomical apex 90 and a radiological apex 91. It is known that devitalization must be done close to the anatomical apex 90 but must not go beyond it, so that the length of the root canal must be measured from the top 93 of the tooth down to the anatomical apex 90, tooth by tooth.

These measurements are obviously necessary because of the great variety of tooth sizes among types of person, age and other factors. The needle 100 already described permits these measurements to be made.

Assuming that a tooth 80 with a caries 88 on the crown 81 has to be treated, an anaesthetic is given and an aperture 95 of a diameter of mm 2–4 is made in the crown 81 until the entrances 96 and 97 to the root canals 84 and 85 (FIG. 3) can be seen.

Said canals are then probed to calculate the necessary depth which must correspond to the entire length of the canal less about 1 mm from its apex.

By using the needle 100 already described it is possible to calculate the length of intervention by electronic means.

For this purpose the push button 22 on the apparatus 10 is pressed and the machine is set for measuring the root canal.

This setting is confirmed by illumination of the pilot light 23. Then, as seen in FIG. 5, the pincer 64 is applied to the lower lip 111 of the patient 110, said pincer being on cable 65 connected to cable 62, after which the needle 100 mounted in the handle 50 is introduced into the root canal to which treatment has to be given, for example the canal 84 (see FIG. 4).

When the tip 105 of said needle 100 reaches the beginning of the apical area, a two-tone warning sound is given.

This signal announces that the correct depth for devitalization has been reached, namely the depth of about mm 1.5 from the apex.

At this point the operator removes the pincer from the lip of the patient who than takes hold of the neutral handle 60 (FIG. 5) and presses the button concerned with the treatment from among buttons 30–33 on the apparatus.

When the right button has been pressed, the apparatus automatically sets the time, power and frequency necessary and automatically passes from the setting for measuring depth to that for distributing energy. The operator then presses the control pedal 70 determining generation, inside the root canal in which the needle is lodged, of an electric pulse sufficient to devitalize said canal.

A single-tone warning signal indicates completion of the treatment.

Power of the current used for this purpose is substantially 70 W RF, at 300 Ohm, high frequency of about 0.5 Mhz and is applied for about one tenth of a second.

After the operation the machine automatically returns to the "measuring" position ready to repeat the cycle.

The pulse of current emitted by the machine acts on the bundle comprising nerves, vein and artery in the canal.

The bundle of nerves is disintegrated and blood in the vein is coagulated at the same time.

Practically speaking the whole of the material in the canal is removed and the canal, as well as its branches (FIG. 4) is sterilized.

The operator then closes the canals with special cement 45 and can treat the caries 88 and complete the filling 46 (FIG. 7).

The whole apparatus is electronically controlled as seen in the block diagram in FIG. 8, This diagram comprises the entry filter 120, feeder 121, RF pulser, generator of pulse radio frequency 122, the circuit 123 for setting output power shown on the display 124, the circuit 125 for setting Burst time, the circuit 126 for passage, by control 127, from manual to automatic operation and vice versa, the circuit 128 that automatically protects the output pulse so that it does not exceed the set power value and the safety circuit 129 that prevents involuntary repetition of the devitalizing process before 10 seconds have passed.

The circuit 130 is an acoustic warning whose two-tone signal warns when the apical point has been reached during measuring, and whose single tone sounds warns that the devitalizing pulse has been applied and the operation completed.

When in its automatic setting the apparatus selects, by buttons 30–33 the type of tooth to be treated and then automatically adjusts power and time for that type of tooth.

Output power can be adjusted with button 24 that acts on the circuit 131.

What is claimed is:

1. A method of devitalizing a tooth, comprising the steps of inserting in a root canal through an aperture extending to an entry of the root canal an electrode in form of a needle connected to an electronic apparatus that generates both an acoustic and visual signal when a tip of the needle is close to an apical hole; generating high-frequency electric pulses; providing a plurality of preset values of power, time and frequency according to a type of a tooth to be treated for selection by the user and selecting a preset value to destroy that part of a vascular nervous tissue in contact with the needle and to coagulate a vascular bundle that has not been destroyed, so that when the tip of the needle is close to the apical hole, the high-frequency electric pulses are generated and transmitted to the tooth by an operator thereby devitalizing the tooth.

2. A method as defined in claim 1; and further comprising placing a socket for a cable that connects an electronic circuit to a metal neutral handle, in contact with a part of a patient's body during a treatment to assist transmission of the high frequency electric pulse to the vascular nervous tissue and the vascular bundle.

3. A method as defined in claim 1; and further comprising applying a pincer connected by a cable to a socket of the apparatus, to a part of a patient's face during measuring.

4. A method as defined in claim 1; and further comprising producing an emission of the high-frequency pulse by a pedal control device.

5. A method as defined in claim 1; and further comprising automatically adjusting the power, time and frequency of the high frequency electric pulse by the electronic apparatus by pressing one of push buttons which corresponds to a type of the tooth which is being treated.

6. A method as defined in claim 1; and further comprising increasing a value of the high-frequency pulse by a control placed on the apparatus.

7. A method as defined in claim 1; and further comprising using the needle composed of stainless steel.

8. A method as defined in claim 1; and further comprising the step of using the needle which has a shaft with a diameter of substantially 1 mm, a rear section with a length of substantially 15 mm, a front section with a length of substantially 5 mm and is bent at an angle of substantially 110° relative to the rear section.

9. A method as defined in claim 1; and further comprising using the needle which is selected from a set including needles of different length with an average length of substantially 30 mm, and also including needles of a tapering structure with a diameter at a base of substantially 0.25 mm and at a tip of substantially 0.1 mm.

10. A method as defined in claim 1; and further comprising using the apparatus which includes a cable for electric feed, a cable for the high frequency electric pulse operated by a pedal, a socket for a cable connected to an active handle of insulating material with a metal core with a head at a front end, into which the needle is insertable and fixable.

11. An equipment for executing a tooth devitalizing process, comprising an electrode in form of a needle insertable into a root canal through an aperture extending to an entry of the root canal; means for generating an acoustic and visual signal when a tip of said needle is close to an apical hole; means for generating high-frequency electric pulses; means for providing a plurality of preset values of power, time and frequency according to a type of tooth being treated for selection by the user, and selecting a preset value to destroy a part of a vascular nervous tissue in contact with the needle and to coagulate a vascular bundle that has not been destroyed, so that when said tip of said needle is close to the apical hole, said high-frequency electric pulses are generated and transmitted to the tooth by an operator thereby devitalizing the tooth.

12. An apparatus as defined in claim 11, wherein said apparatus includes input filters, a feeder, a pulser for generation of the high frequency electric pulse, a circuit for setting an output power, a circuit for visualizing power on a display, a circuit for setting Burst time, a circuit for changing over from manual to automatic operation and vice versa, a circuit for protection against an increase in a value set for output power, a safety circuit for preventing an involuntary repetition of a devitalizing operation before a set time has passed, a circuit for a two-tone acoustic warning to be sounded when during a measuring stage a tip of the needle reaches an apical hole, and a signal-tone warning to indicate that the high frequency electric pulse has taken effect and an operation has therefore been completed.

* * * * *